(12) United States Patent
Baruch

(10) Patent No.: US 8,100,835 B2
(45) Date of Patent: Jan. 24, 2012

(54) ARTERIAL PULSE DECOMPOSITION ANALYSIS FOR VITAL SIGNS DETERMINATION

(76) Inventor: Martin Baruch, Charlottesville, VA (US)

( * ) Notice: Subject to any disclaimer, the term of this patent is extended or adjusted under 35 U.S.C. 154(b) by 1434 days.

(21) Appl. No.: 11/500,558

(22) Filed: Aug. 8, 2006

(65) Prior Publication Data

US 2011/0288419 A1     Nov. 24, 2011

Related U.S. Application Data

(63) Continuation-in-part of application No. 10/502,932, filed on Jul. 29, 2004, now Pat. No. 7,087,025.

(51) Int. Cl.
*A61B 5/02* (2006.01)
(52) U.S. Cl. .................. 600/485; 600/500; 600/504
(58) Field of Classification Search .......... 600/481–507
See application file for complete search history.

(56) References Cited

U.S. PATENT DOCUMENTS

| | | | | |
|---|---|---|---|---|
| 4,796,184 A | * | 1/1989 | Bahr et al. | 600/492 |
| 5,533,511 A | * | 7/1996 | Kaspari et al. | 600/485 |
| 6,004,274 A | * | 12/1999 | Nolan et al. | 600/486 |
| 6,325,761 B1 | * | 12/2001 | Jay | 600/485 |
| 7,283,865 B2 | * | 10/2007 | Noren | 600/518 |
| 2008/0255463 A1 | * | 10/2008 | Chowienczyk et al. | 600/486 |

* cited by examiner

*Primary Examiner* — Miranda Le
*Assistant Examiner* — Karen Toth
(74) *Attorney, Agent, or Firm* — Sheldon H. Parker

(57) ABSTRACT

Determining physiological life signs, with a sensor that is in contact with the surface of a patient's skin at point proximate an artery, and measuring arterial blood vessel displacement and/or blood pressure changes. A data stream of measurements of is collected and a set of parameters from the collected data, a number of physiological life signs parameters, is extracted from the data. The physiological life signs that can be extracted include heart rate, breathing rate, systolic blood pressure, and diastolic blood pressure.

15 Claims, 25 Drawing Sheets

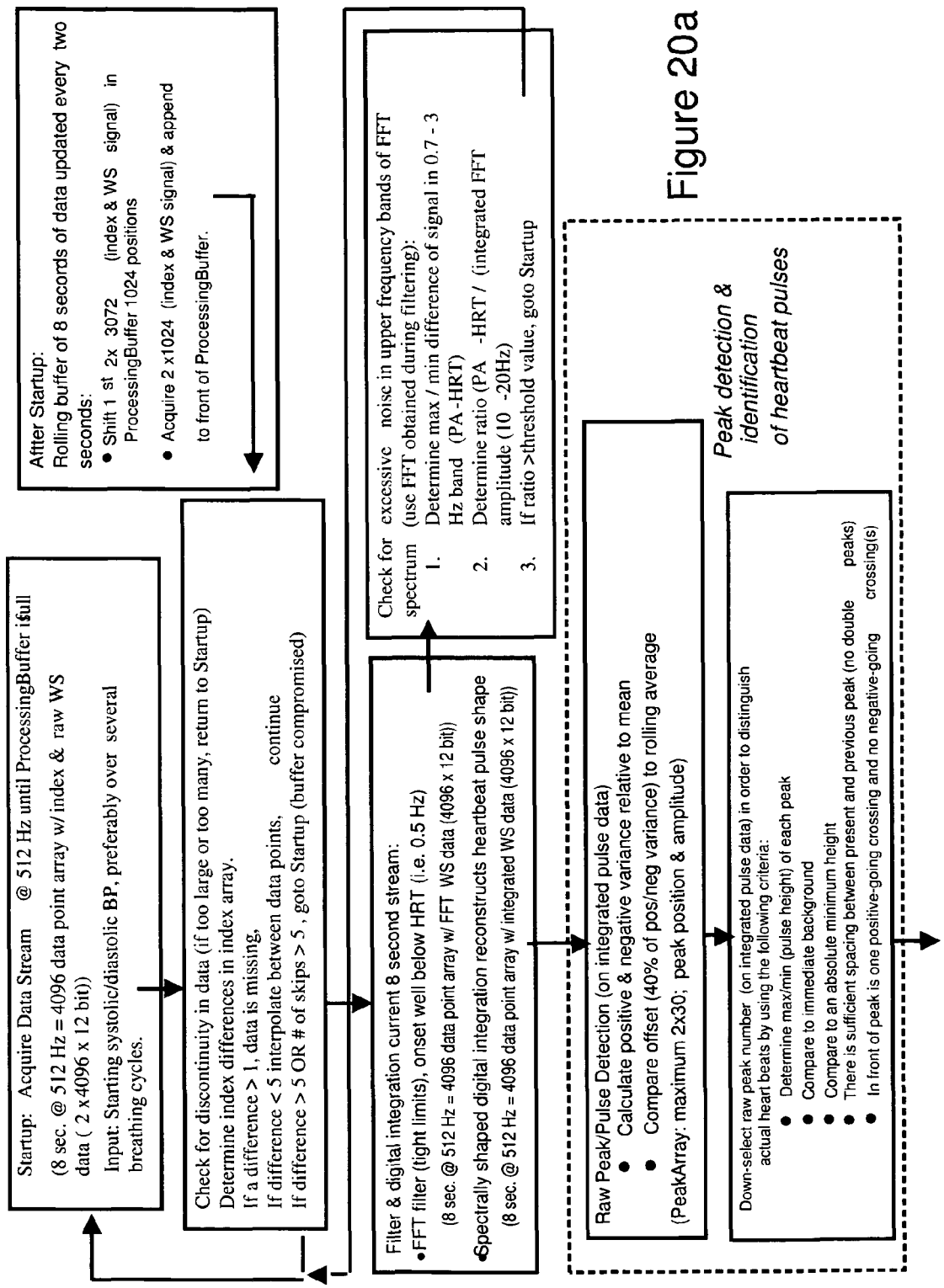

Determine pulse analysis parameters for each peak :
- Peakposition/frequency
- P1N1 (=time difference P1-N1)
- N2N1 (= time difference N2-N1)(6$^{th}$ derivative)
- P2 N1 etc. (6$^{th}$ derivative)
- N3N1 (6$^{th}$ derivative)
- P3N1 (4$^{th}$ derivative)
- N4N1 (4$^{th}$ derivative)
- P1 amplitude (from integrated data)
- P2/P1 amplitude ratio (calculated from 6$^{th}$ derivative data)
    - (Pulse height2/pulse width2/ frequency) / (Pulse height1/pulse width1/ frequency)

P3/P1 amplitude ratio (calculated from integrated data w/ positions from 4$^{th}$ derivative
    - P3 amplitude/P1 amplitude
- WS peak height Physiological parameters determination:

Heart rate – derived from interbeat interval

Breathing rate power spectrum of N1P2 for adjacent heartbeats (requires interpolation of unevenly spaced data points onto evenly spaced time grid (or Lomb Scargle periodogram)

Systolic BP - use P2/P1 amplitude ratio to establish pressure trend
relate T13 linearly to systolic pressure (i.e. gain, gain sign, & offset calculated from initial BP values )
Diastolic BP -using systolic BP result and pulse pressure calculated from P2/P1
calculate diastolic pressure by subtracting pulse pressure from systolic BP result.
Mean arterial pressure

Figure 20c

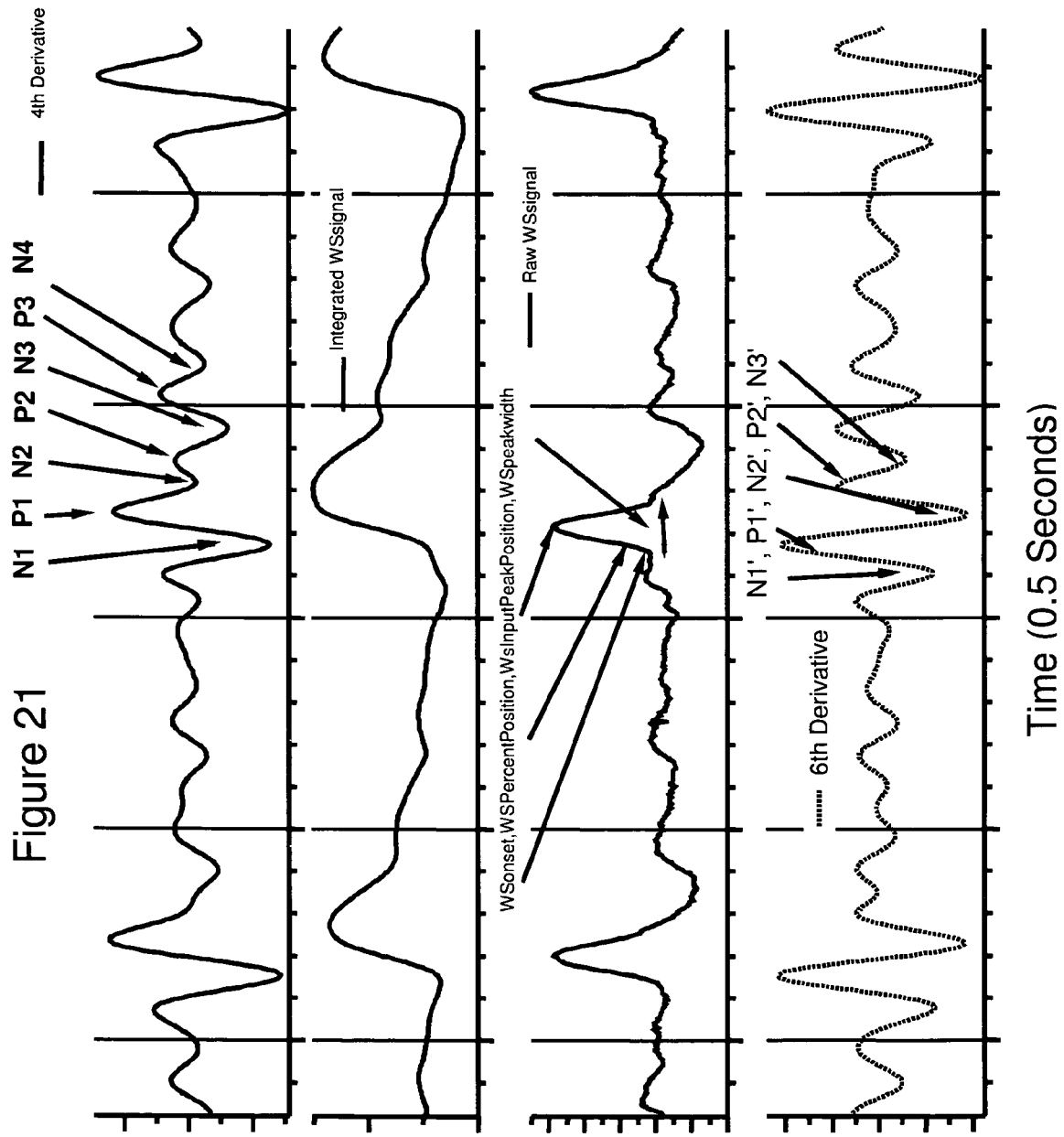

ARTERIAL PULSE DECOMPOSITION ANALYSIS FOR VITAL SIGNS DETERMINATION

CROSS-REFERENCE TO RELATED APPLICATIONS

This application is a continuation-in-part of U.S. patent application Ser. No. 10/502,932, filed Jul. 29, 2004 now U.S. Pat. No. 7,087,025, entitled, "Blood pressure determination based on delay times between points on a heartbeat pulse", which application claims the benefit of provisional application 60/352,213 filed Jan. 29, 2002, 60/371,399 filed Apr. 11, 2002; 60/387,435 filed Jun. 11, 2002, and 60/410,349 filed Sep. 13, 2002, all of which are incorporated herein by reference.

GOVERNMENT INTEREST STATEMENT

ONR (Office of Naval Research) N00014-04-C2-0204

BACKGROUND

1. Field of the Invention

This invention is concerned with the measurement of blood pressure (BP), and more particularly with deducing arterial blood pressure from a time-dependent analysis of the arterial pulse.

2. Background of the Invention

There have been many attempts to deduce arterial blood pressure from the time-dependent analysis of the arterial pulse, as opposed to an amplitude-dependent analysis, which cuffs, tonometers etc. use. The primary advantages of a time-based blood pressure monitoring system over one based on amplitude analysis are wearer comfort and inherent calibration. Amplitude-dependent devices have to couple to the pressure wave within the artery and they have to closely track the coupling force with which they bear down on the artery. The required partial occlusion of the artery frequently leads to distinct skin markings as well as numbness of the hand when the radial artery is monitored, which is the most commonly used site for non-invasive blood pressure monitors. In addition, if the device loses track of the force with which it bears down on the artery, either because of drastic blood pressure changes or because of signal-disrupting movements, it has to be re-calibrated. If this requires inflation of a cuff, such as is the case with the Colin Pilot unit, the wearer will experience additional discomfort.

Previous attempts to deduce blood pressure from arterial pulse time domain analysis have used the well-known fact that the propagation velocity of the arterial pulse is highly dependent on the arterial pressure. These approaches have used delay times between arterial pulses measured at different arterial sites, such as the brachial and the radial artery pulse sites, or, most commonly, have used the time delay between the QRS complex of an ECG signal and a pulse measured at an arterial pulse site.

In general, such two-site approaches have only been able to track substantial changes in BP using pulse transit time (PTT) but have failed to reliably resolve small changes in BP. An example of a small change in BP that is physiologically important is Pulsus Paradoxus (PP), which is defined as the abnormally large decline in systemic arterial pressure and pulse pressure associated with inspiration, usually due to an airway obstruction such as during an asthma attack.

A further and significant complication in previous PPT measurement approaches has been the determination of the diastolic and systolic BP components. The pulse location in time has usually been determined by establishing a threshold condition near the foot of the arterial pulse, either using a simple percentage of total pulse height rule or other more sophisticated methods, such as the tangent intersection method, which is the intersection of the straight-lines drawn through the rear and the fore-fronts of the arterial pulse wave. Not surprisingly, given the fact that the threshold point is close to the diastolic pressure amplitude range, delay times obtained in this manner have correlated reasonably well with diastolic blood pressure changes.

However, two-site measurement approaches have been especially deficient in the measurement of systolic blood pressure variations. This is not surprising because the heartbeat pressure pulse changes dramatically in shape and amplitude as it heads toward the arterial periphery. As a result attempts to compare the time delay evolution of certain points on the pulse measured at different arterial pulse sites, aside from foot-to-foot measurements, have been difficult. The changes in pulse shape are due to a number of factors, including changes in the arterial wall material composition that affect the-wall's elastic behavior, the taper of the main arterial branch, the distribution of branch lines, and pulse reflections. The result is that the pulse steepens and contracts as it propagates. More importantly, due to the fact that reflected pulses readily propagate through the arterial system, the pulse measured at a certain arterial site is actually a superposition of a number of different and distinct pulse components. Therefore, knowledge of these pulse components and how they travel through the arterial system as a function of blood pressure is essential to make meaningful pulse time delay measurements for the purpose of blood pressure determinations.

In the absence of a comprehensive physical understanding of the structure of the pulse in the arterial periphery it is therefore not surprising that commercially viable time-domain analysis approaches of the arterial pulse have so far limited themselves to the determination of arterial pulse propagation velocities alone.

SUMMARY

An object of the present invention is to avoid the problems and disadvantages of multiple-site blood pressure measurements and to provide single-site measurement of blood pressure with less complexity and lower cost than has heretofore been possible.

It has now been discovered that a well known pressure-velocity relationship that has been shown to hold for pressure-change induced pulse propagation changes also holds for the components of a single arterial pulse. In addition it has been determined that the component pulses of which the arterial pressure pulse is comprised, can be distinctly determined. Knowledge of where these component pulses originate, what arterial distances they have traversed, as well as their measured relative time delays makes it possible to determine the blood pressures, both systolic as well as diastolic, that influenced their relative delay times.

In contrast with the foregoing systems, a time-based arterial pulse analysis approach is less dependent on the coupling pressure to the arterial pulse. As long as the sensor is linear as well as sensitive enough to record the entire arterial pulse shape with high fidelity, it is possible to deduce from the time evolution of the arterial pulse the blood pressure to which the pulse is subjected. Since such a device does not have to couple to the artery's pressure wave as aggressively, wearer comfort is increased. In addition, by using algorithms that are based on a physiological model of the arterial pulse, the approach is neither subject to continued re-calibrations after motion has occurred, nor otherwise induced disruptions of the signal. This is due to the fact that a time-based arterial pulse analysis approach constitutes tracking the time evolution of physiologically relevant markers in the arterial pulse. As long as the algorithm re-acquires the time positions of the relevant markers, the original calibration that linked diastolic and systolic as well as mean blood pressure components to the time markers will hold. The goal has been somewhat elusive up until now because of the uncertainty of determining physiologically relevant arterial pulse markers.

In accordance with a first broad aspect of the present invention blood pressure (BP), and more particularly non-occlusive, passive blood pressure, is measured using a sensor of heartbeat pulses at a single site, and with a resolution sufficient to resolve small variations in blood pressure. The invention utilizes a primarily time-dependent pulse wave analysis that is based on a physiological model of the components of the arterial pulse.

In accordance with a further aspect of the present invention, the problems due to different pressure-induced pulse-shape modulations associated with different pulse detection sites are avoided by detection of single heartbeat pulses at a single site and by analysis of individual pulses.

In accordance with another aspect of the invention use is made of the fact that changes in time delay between certain different parts of a heartbeat pulse, subjected to different arterial pressures, reflect changes in blood pressure.

BRIEF DESCRIPTION OF THE DRAWINGS

The invention will be further described in conjunction with the accompanying drawings, which illustrate preferred embodiments, and wherein:

FIG. 21 shows an example of a section of the ETC wrist sensor's data ($3^{rd}$ graph from top) as well as the results of integration ($2^{nd}$ from top), $4^{th}$ differentiation of the integrated signal (top graph), and $6^{th}$ differentiation (bottom graph).

DETAILED DESCRIPTION OF THE INVENTION

Definitions

Figure 1:
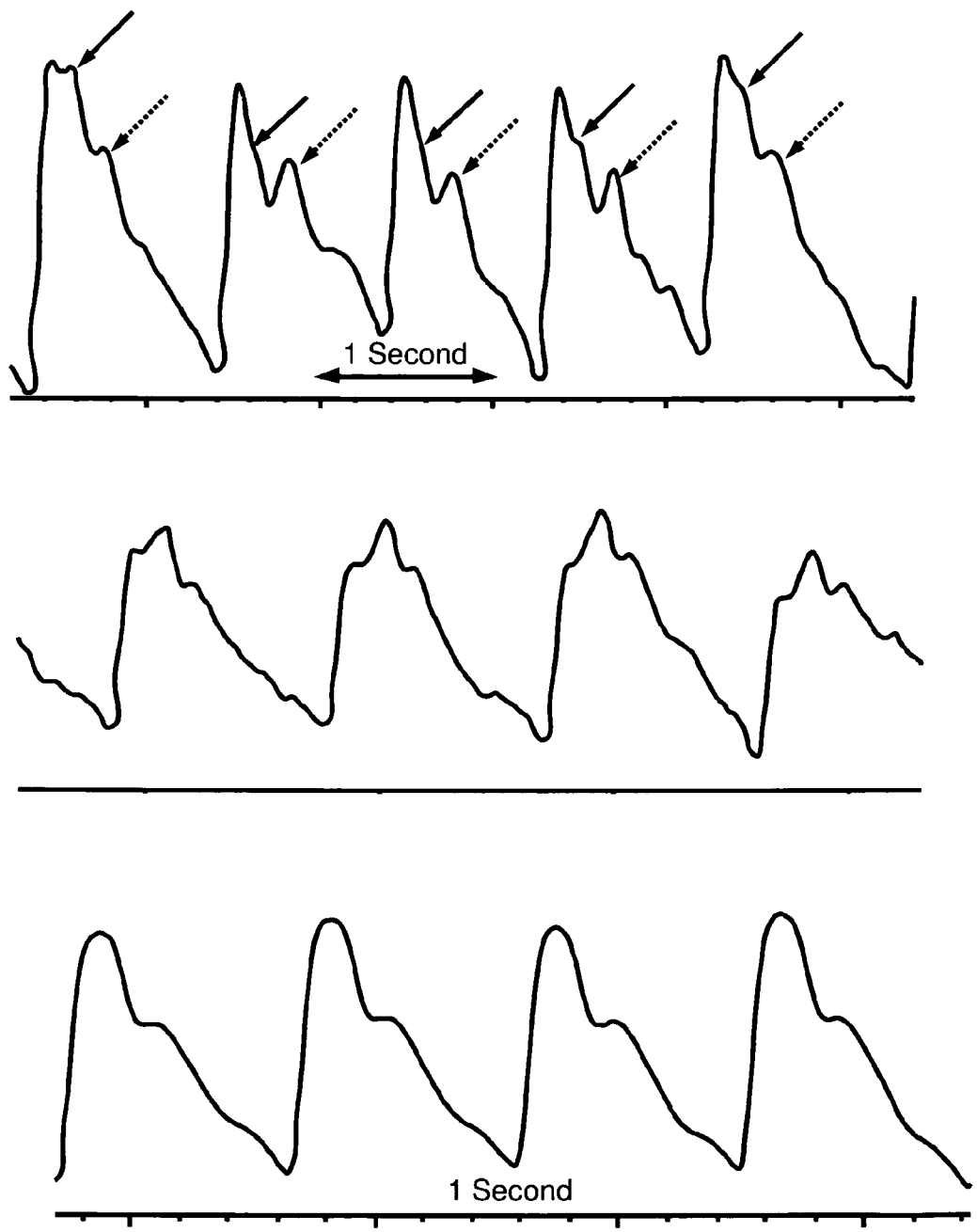
FIG. 1 shows examples of high-fidelity radial arterial pulse shapes recorded with an Empirical Technology Corporation, (ETC) wrist monitor.

Where the definition of terms departs from the commonly used meaning of the term, applicant intends to utilize the definitions provided below, unless specifically indicated.

For the purposes of the present invention, the term "plethysmograph" refers to an instrument that measures variations in the size of an organ or body part on the basis of the amount of blood passing through or present in the part.

For the purposes of the present invention, the term "Valsalva episode" or "Valsalva maneuver" refers to the expiratory effort when the mouth is closed and the nostrils are pinched shut, which forces air into the eustachian tubes and increases pressure on the inside of the eardrum, and to the expiratory effort against a closed glottis, which increases pressure within the thoracic cavity and thereby impedes venous return of blood to the heart. Essentially, Valsalva maneuver is any attempted exhalation against a closed glottis or against a closed mouth and nose.

A Valsalva maneuver performed against a closed glottis results in a drastic increase in pressure in the thoracic cavity, the airtight section of the torso that houses the lungs and heart. In normal exhalation, the diaphragm relaxes, pushing up and into the thoracic cavity. This increases pressure in the cavity and forces the air out of the lungs. However, when the air cannot escape, as when the glottis is closed in a Valsalva maneuver, pressure simply continues to build inside the thoracic cavity until the diaphragm relaxes or the air is allowed to escape. This reduces the amount of blood flow into the thoracic cavity, especially in the veins leading to the right atrium of the heart.

For the purposes of the present invention, the term "inter-beat interval" refers to the time interval between temporally adjacent heartbeat pulses.

For the purposes of the present invention, the term "monotonically" refers to the designating of sequences, the successive members of which either consistently increase or decrease but do not oscillate in relative value. Each member of a monotone increasing sequence is greater than or equal to the preceding member; each member of a monotone decreasing sequence is less than or equal to the preceding member.
Description Before describing the details of the invention it is necessary to provide an overview of the physiological model that underlies the approach of the invention. The benefit of the model is that it provides a physiological understanding of the structure of the arterial radial pulse as a result of which arterial pulse analysis algorithms can be developed based on a physical model of the arterial tree, as opposed to for example, implementing a multi-variable mathematical model that correlates newly acquired pulse shapes with a large set of previously stored pulse shapes, or using a generalized transfer function to reverse the filtering effect of the arterial tree on the propagating arterial pulse. While the description given here is limited to applying the model to the radial arterial pulse, it will become clear in the context of the description of the model that it can readily be extended to other pulse sites.

A Model of the Radial Pulse

At the core of the model is the concept that the radial arterial pulse is a superposition of several component pulses. At the temporal front of the radial pulse envelope is the primary pressure pulse that results from the contraction of the left ventricle and the subsequent ejection of blood into the arterial system. Additional component pulses give rise to the temporal features of the radial arterial pulse that follow this primary pulse. Isolation and identification, with regard to time and amplitude, of these individual component pulses provides an analysis from which information about blood pressure as well as arterial tree health can be obtained.

Background

A basic understanding of the physical circumstances of the propagation of the arterial pulse from the heart to the periphery was achieved decades ago. The picture is one of an arterial pressure pulse that originates at the interface of the left ventricle and the aortic root traveling away from the heart through the arterial tree and being reflected at various sites to various degrees. The reflection sites are areas where the arterial tree branches or where different diameter sections join. Both types of sites present an impedance mismatch to the propagating arterial pulse, giving rise to reflections. The existence and the physiological consequences of reflections in the arterial tree are now commonly accepted. One example is the "diastolic wave" which is clearly a reflection phenomenon. In young and elastic arterial trees this reflection arrives back at the heart well into the diastolic phase of the cardiac cycle and has the beneficial effect of raising the blood pressure outside the closed left ventricle, thereby enhancing perfusion of blood into the coronary arteries. As the arterial tree ages and hardens, pulse velocities increase and reflections arrive earlier. Pathologies arise when the reflections arrive while the left ventricle is still open. The heart now has to contract harder to overcome the additional pressure in the aortic root, leading to wall-thickening and other complications. Also, since the pressure in the aortic root is now lower during the diastolic phase, perfusion of the coronary arteries is diminished.

The above description of the existence of reflections and their physiological impact is well established in the medical literature. Extensive clinical studies and theoretical modeling efforts have been performed to investigate various aspects of arterial pulse reflections, such as the "second systolic peak", yet no clear model with regard to the radial arterial pulse has been proposed as to where exactly the reflections arise. As an example, O'Rourke (1) proposes an asymmetric T-shaped model where the pulse originates at the T junction and the ends of the T represent generalized reflection sites of the lower body and the upper body. The model does a reasonable job in explaining the shape of the aortic pulse that has been analyzed in detail in a number of clinical studies but it draws no conclusions about what effect these findings should have on the shape of the pulse in the arterial periphery, such as the radial pulse.

To begin, why is it reasonable to assume that there are distinct reflection sites in the arterial tree as opposed to the assumption that, as an example, "the lower body" as a whole gives rise to the reflections that have such physiological significance to cardiac health? The answer is two-fold. One is that the features of the reflected wave are too distinct, and too sharp, as to be the convolution of different reflections originating from different sites with different time delays and different reflection coefficients, which would tend to broaden out specific pulse features. The second answer is that the arrival times of the specific features of the radial pulse very much narrow the location possibilities of the reflection sites that gave rise to them.

FIG. 1 presents a series of radial pulse signatures collected with the ETC wrist pulse sensor from different individuals of different ages. The wrist pulse sensor is described in provisional patent application, serial number US60/800,521, filed May 15, 2006 for a Wrist Plethysmograph, the disclosure of which is incorporated by reference as though recited in full.

Figure 2:
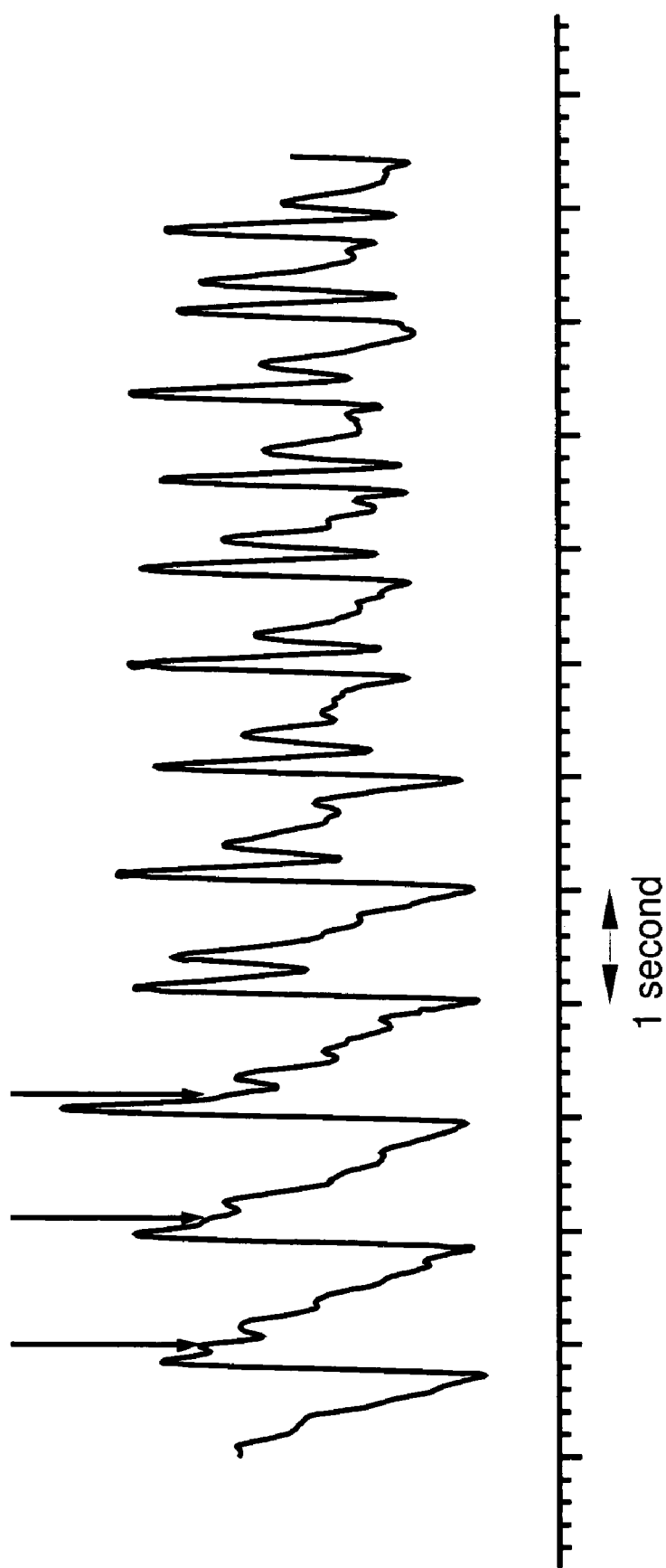
FIG. 2 shows a radial pulse during onset of Valsalva maneuver, in which the vanishing of the second systolic pulse can be seen.
Figure 3:
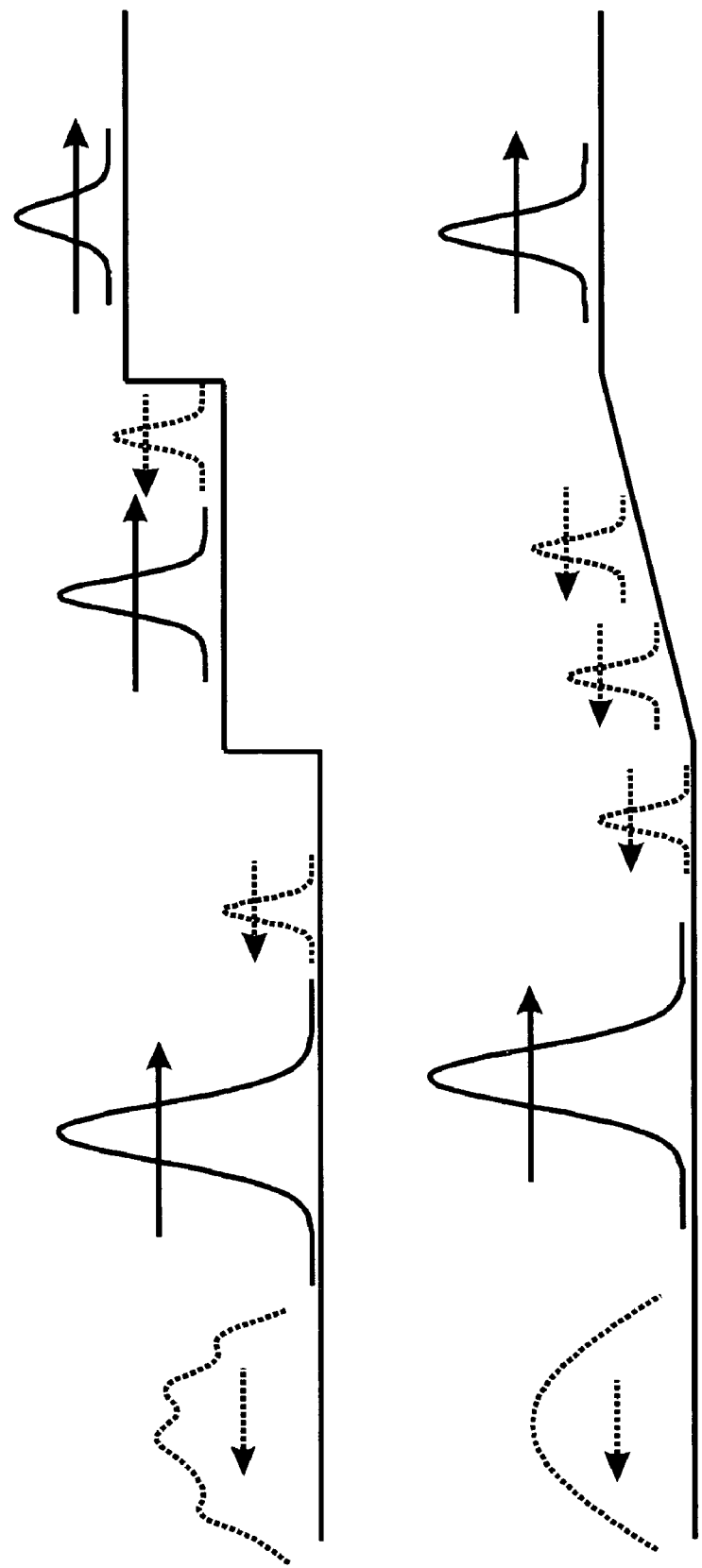
FIG. 3 shows a qualitative comparison between reflected pulse (left pointing arrow) resulting from distinct reflection sites (top) as compared to a reflected pulse resulting from distributed, amorphous reflection sites.

One feature almost all of the radial pulse signatures share is the fact that they exhibit pulse-like protrusions that have a time duration comparable to that of the primary pulse. Data that clarifies this point is presented in FIG. 2, which presents radial pulse data collected during a Valsalva episode. One consequence of Valsalva is the shortening of the cardiac ejection period as a result of which it is possible, in a comparatively young and elastic arterial tree, to see the complete separation of primary pulse and reflected pulse. Clearly the reflected pulse shows next to no broadening compared to the primary systolic peak, supporting the hypothesis that it originated at a distinct refection site. FIG. 3 seeks to clarify this point further. While a distinct reflection site will give rise to a reflection that bears strong resemblance to the primary pulse, distributed and multitudinous reflection sites will give rise to a plethora of reflected pulses, arriving at different time delays and with different amplitudes. The superposition of such a system of reflection sites will be a featureless, broadened pulse. The presence of distinct pulse-like features in most of the radial signatures shown therefore suggests that, past the primary systolic peak, distinct reflection sites are responsible for the sequence of reflected pulses that comprise the "diastolic wave".

Figure 4:
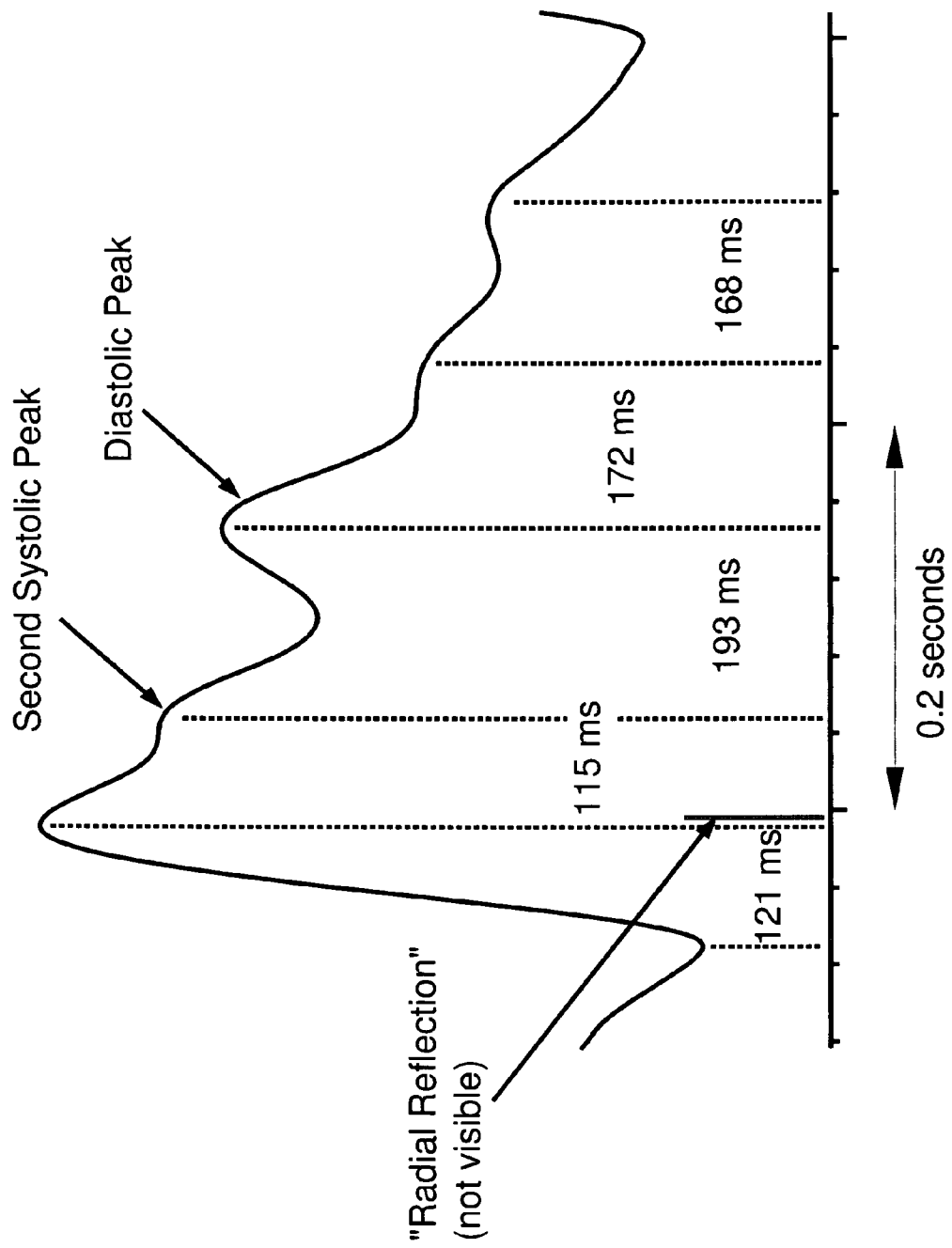
FIG. 4 shows the distinct pulse structure in the radial arterial pulse of a 44 yr. male.

While the presence of distinct pulse-like features in the radial pulse suggests the existence of distinct reflection sites, their time of arrival relative to the primary pulse makes the argument significantly more concrete. FIG. 4 presents an example of the radial pulse of a 44 year old male as well as the time intervals between its various component pulses. The first timing issue worth considering is to what degree the pulse features are influenced by the geometry of the arm, that is, could one of the pulse features observed be due to a reflection site in the arm? Arterial pulse velocities in the radial artery are on the order of 7-8 m/s. Since the pulse signal is collected at the wrist, the distance from that site to a site of a potential reflection, the interface between artery and arterioles at the wrist, is on the order of centimeters. Therefore the reflection would return in a matter of a few milliseconds, as indicated in FIG. 4 by a short vertical line in the immediate vicinity of the primary pulse. Since all the reflected pulse features in the radial pulse appear at far greater time delays, as indicated in the Figure, they have to originate elsewhere in the arterial tree.

Figure 5:
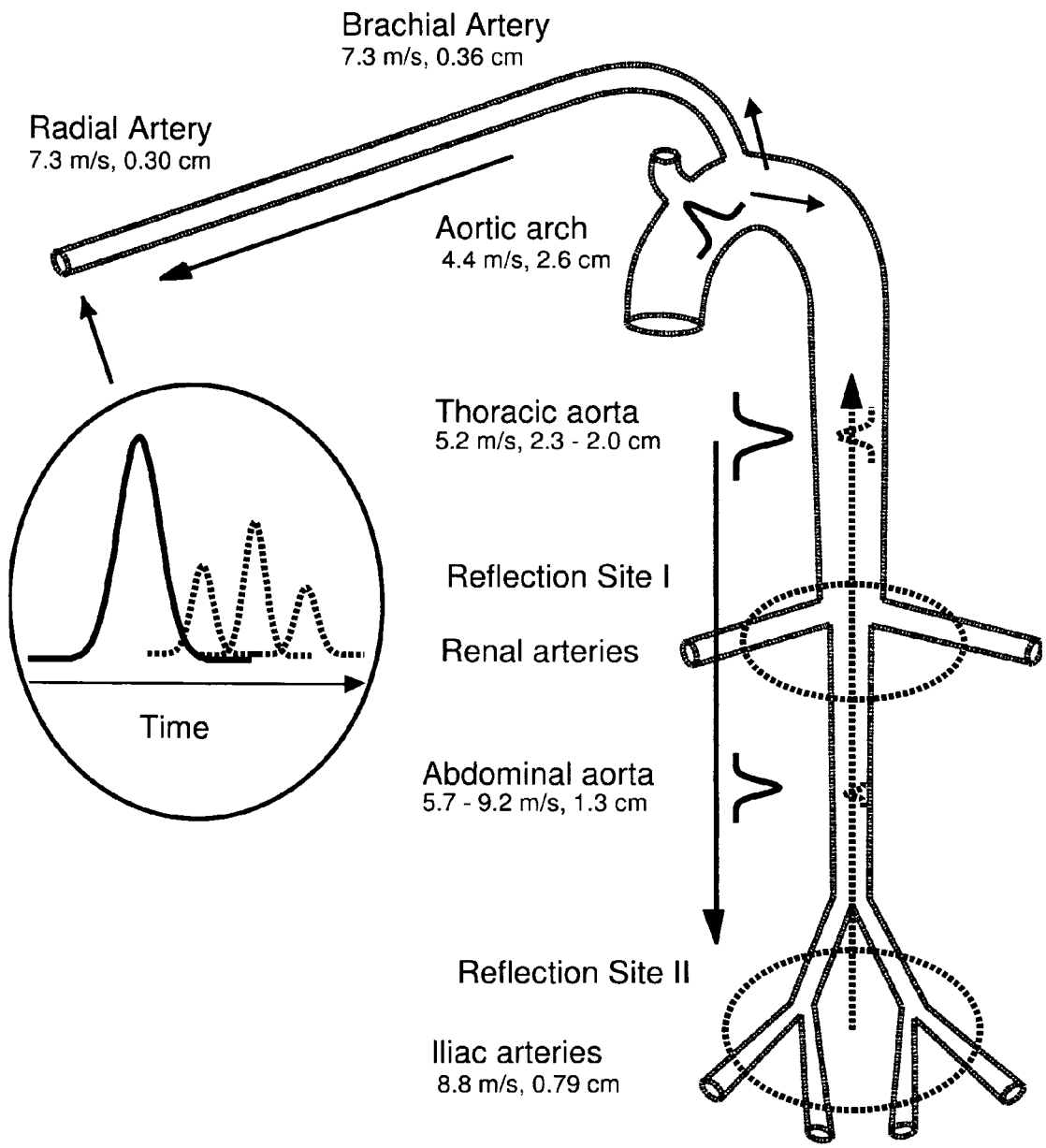
FIG. 5 shows a sketch of the aorta and the left arm arteries.

Since arterial pulse propagation velocities have been measured throughout the body, it is possible to match time delays with potential reflection sites. FIG. 5 presents a simplified sketch of the components of the aorta as well as the connecting arteries of the legs and the left arm. The sketch also lists typical arterial diameters as well as arterial pulse propagation velocities at the different sites as published in the medical literature. If one uses approximate arterial distances and their respective velocities, the "second systolic" peak matches readily with the site labeled "reflection site I" while the third peak matches with "reflection site II". In light of results published twenty years ago these conclusions are not surprising.

In 1985 Latham (2) performed a detailed experimental study to map out the shape of the pressure pulse in the different sections of the aorta using a specially designed catheter with spaced micromanometers. His work clearly demonstrated the existence of two major reflection sites to the downward traveling arterial pulse, one being in the region of the renal arteries, the other beyond the bifurcation of the iliac arteries.

At the location of the renal artery the diameter of the aorta, which tapers continuously away from the heart, undergoes its greatest change. This discontinuity presents a significant impedance mismatch to the traveling pressure pulse, as a result of which an appreciable part of its amplitude is reflected. The reflection can be reduced using the Valsalva maneuver, which involves exhaling into closed airways. As a result of the increasing pressure within the thoracic cavity the diameter of the thoracic aorta decreases (on the order of 17% as Latham verified ultrasonically). The maneuver therefore alleviates the aortic diameter change at the renal arteries, which reduces the impedance mismatch, thereby lowering the site's reflection coefficient.

Latham also found a second reflection site beyond the bifurcation of the iliac arteries, the contribution of which to arterial pulse reflections in the aorta were ascertained using manual femoral artery occlusion maneuvers. Other contributions to the tail end of the aortic pulse were attributed to diffuse arterial pulse reflections from the periphery.

In view of Latham's work it therefore seems very likely that the two peaks visible past the systolic peak originate at the reflection sites indicated. Valsalva experiments performed as part of this work further support the model. FIG. 2 shows the evolution of the radial pulse during the maneuver, which lowers the reflection from the renal reflection site. The vanishing of the "second systolic peak", which is marked by a vertical arrow while visible, is clearly visible.

The next peak in the radial pulse, that is, the "diastolic peak", as well as the peaks that follow likely arise from the iliac arteries reflection site and not, as Latham had proposed, due to diffuse reflections from the arterial periphery. Latham's explanation with regard to the structure appears to be unlikely, given the distinct peak structure with a spacing comparable to that of the "second systolic" and the "diastolic" peak. Furthermore, the time delay of such reflections would extend up to 250 ms past the "diastolic" peak if some of them truly traversed the length of the legs. Indeed, recent work supports the hypothesis that the peaks visible past the "diastolic" peak are in fact due to re-reflections between the two reflection sites, a reasonable proposition given the strength of the sites' reflection coefficients (10-15% in the case of the renal arteries reflection site, up to 30% in the case of the iliac arteries reflection site).

J. Kriz et. al. (3), showed that it is possible to use force plate measurements as a noninvasive method to perform ballistocardiography, the motion of the body associated with heart activity, by displaying the motion of the heart muscle and the subsequent propagation of the pulse wave along the aorta and its branches. With subjects lying horizontally on a bed that was placed on a force plate they were able to identify the ground reaction forces arising from such center-of-mass altering events as the heart muscle contraction as well as the resulting blood pulse flow. The resolution of the apparatus was sufficient to clearly resolve events involving the re-direction of momentum of the propagating arterial pulse, such the pulse's traversal of the aortic arch, its partial reflection at the renal artery site, the iliac reflection site, as well as the subsequent re-reflections of the reflected pulses. As an aside, in subjects with an aortic aneurism, the site of the arterial distension was clearly identifiable due to its effect on the neighboring "normal" reflection sites.

The basic model of the radial arterial pressure pulse is therefore one of a convolution of the primary systolic peak, its single-pass reflections from the renal arteries and iliac arteries reflection sites, as well as their double-pass re-reflections. The basic schematic of the pulse paths is displayed in FIG. 6. The changes in time delay are clearly demonstrated by FIG. 7, which shows the evolution of the time delay between the front end of the #1 pulse (primary systolic) and the #2 and #3 pulses during the course of a Valsalva maneuver. A dramatic narrowing of the time delay between the primary #1 and the #3 pulse is evident (as well as the #2 pulse while it is visible). In order to understand the details of this time delay contraction, one has to be able to determine the arrival times of the individual component pulses at the wrist independently of each other, that is, an "external" clock, as opposed to one started at the onset of a given radial pulse, is required to time the separate arrivals.

Figure 8:
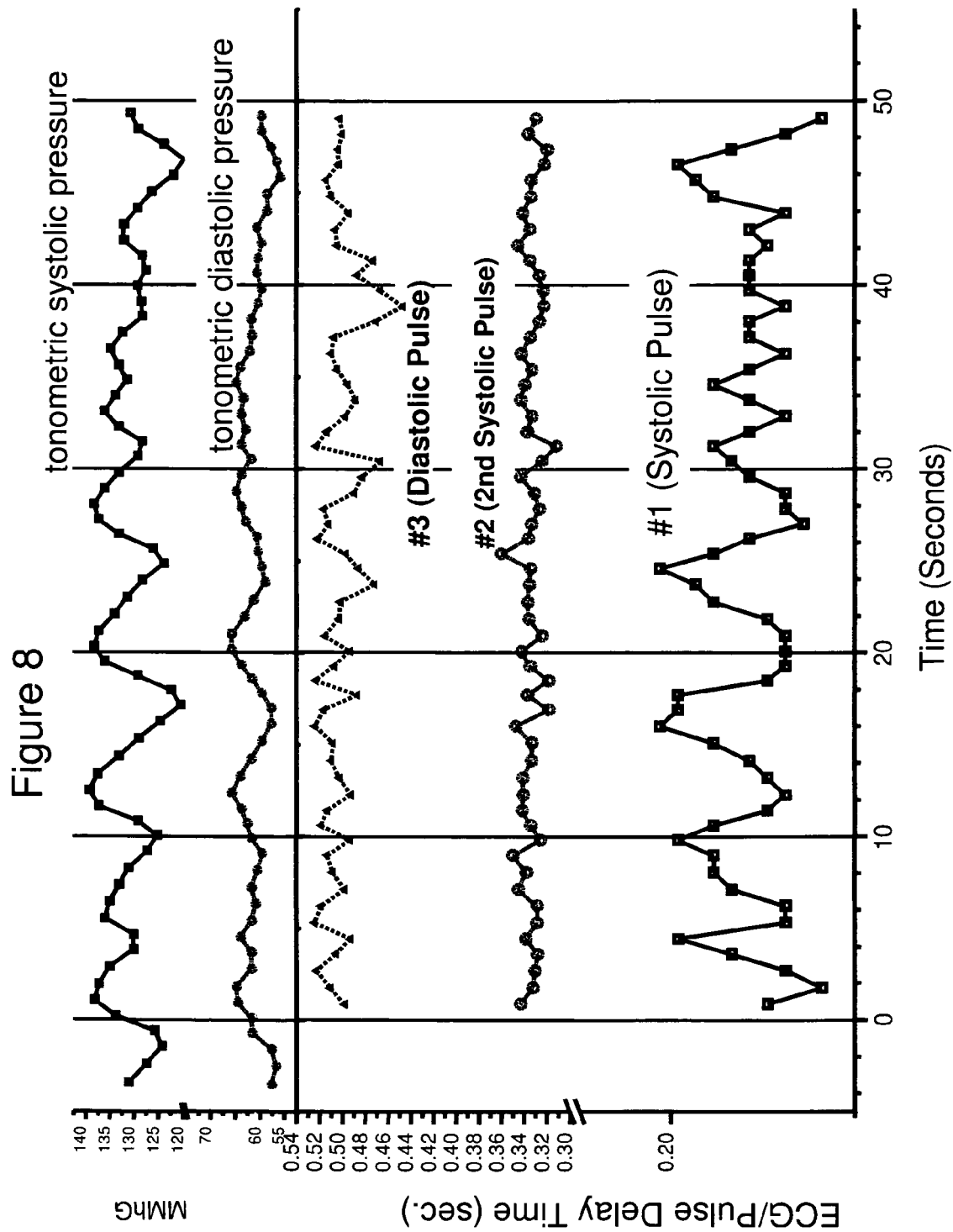
FIG. 8 shows graphs of the inter-beat interval and the time delays of the three constituent pulses relative to an ECG signal during rest.

One means of establishing an "external" clock is to use an ECG signal relative to which the arrival time of each component pulse at the radial artery is measured. Using the Colins Pilot tonometric blood pressure monitor, a subject's ECG and blood pressure was collected in addition to the wrist sensor signal in real time during periods of rest and during the course of a Valsalva maneuver. FIG. 8 gives an example of a 50 seconds long base line during rest. The scale of the #1 pulse has been expanded to enhance the detail of the trace. It is clear from the graph that the systolic peak accelerates and decelerates as the arterial systolic pressure rises and falls with inspiration and expiration. As one would expect, the oscillations in the delay time of the #1 pulse mirror the pressure oscillations. This is to be expected since pulse travel time and pressure are inversely related. In contrast to the #1 pulse, the delay time of the #2 pulse is far steadier, showing no obviously matching modulations. This is also to be expected because the #2 pulse, after traveling to the renal reflection point at systolic pressure, returned as a reflection at a much lower pressure. It also traversed only the softest part of the aorta, the section above the renal reflection point. Consequently, its velocity will be least affected by arterial pressure changes. In line with this, one would expect the #3 pulse to exhibit a higher sensitivity to changing blood pressure environments. From the Kriz experiments it appears that the iliac reflection is a far more pronounced reflection site than the renal site (as a result of which the #3 peak is also usually significantly larger in amplitude than the #2 peak in the radial arterial pulse spectrum. Consequently, the #3 pulse, which on its primary path to the iliac reflection site, traversed the stiffer and therefore faster abdominal aorta as well as the fast iliac arteries, and returns as a reflection at a higher pressure and therefore higher velocity, compared to the #2 pulse. Traveling at a higher pressure subjects the #3 pulse, similarly but not quite as strongly as the #1 pulse, to the steeper part of the arterial non-linear relationship between pressure and velocity.

Figure 9:
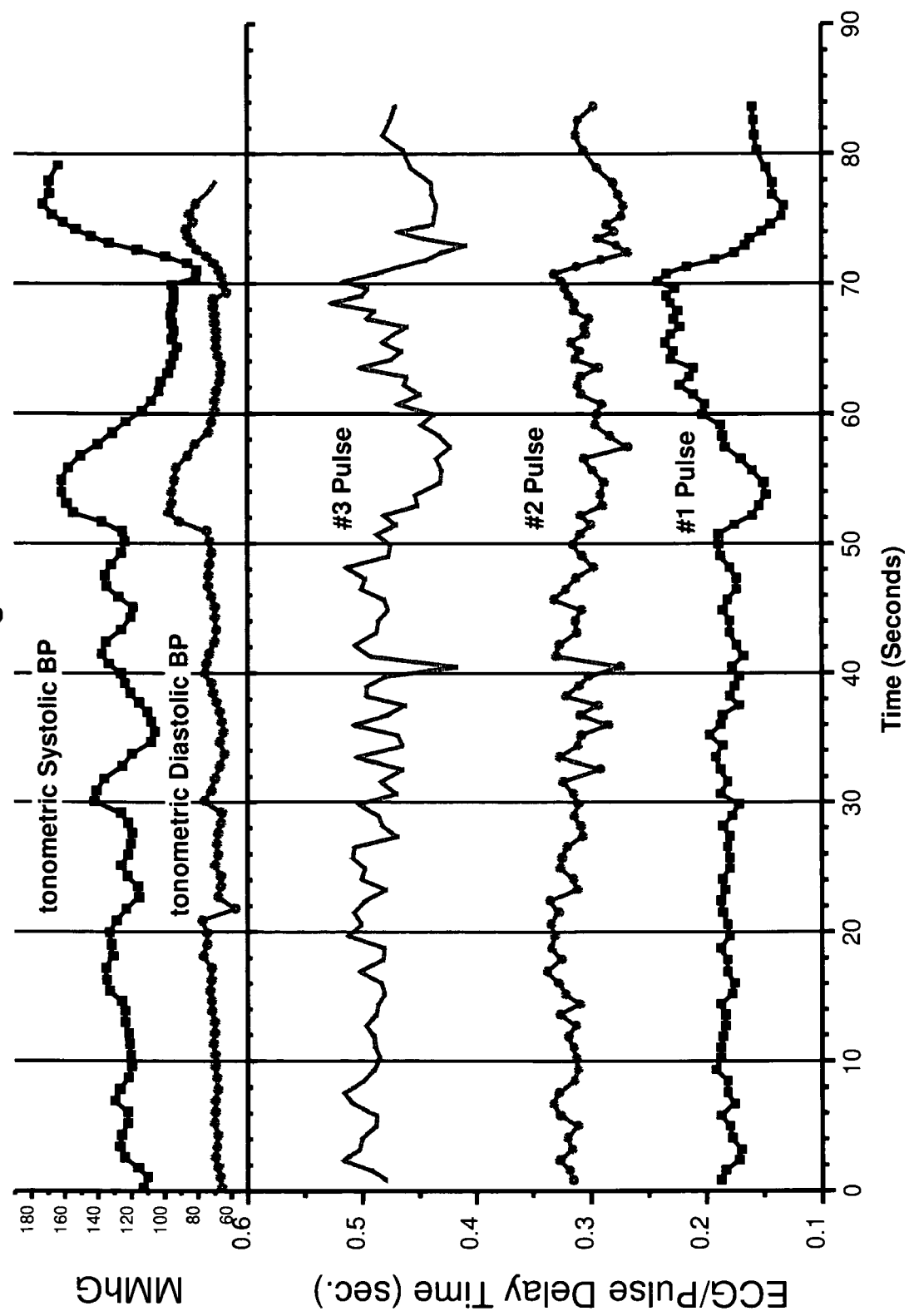
FIG. 9 shows graphs of the inter-beat interval and the time delays of the three constituent pulses relative to an ECG signal during a Valsalva episode.

FIG. 9 presents the results for a Valsalva episode (starting at 50 seconds). Again, the relative immunity of the #2 pulse, as compared to the time delay changes experienced by the other two pulses, is evident. In this case, the reason is slightly different. Due to the pressurization of the thorax during Valsalva maneuver, the thoracic aorta is prevented from expanding. In fact, based on Latham's results, it shrinks. With the arterial wall prevented from stretching, the Young's modulus remains approximately constant and very little change in pulse propagation velocity is observed for the component pulse that spends the longest portion of its travel time in the thoracic aorta, which is pulse #2. With regard to the arrival times of the #1 and #3 pulses it is clear from the graphs that they mirror the shape of the blood pressure curves recorded by the Colin monitor, specifically the systolic curve. In the case of the #1 pulse the reason is obvious. In the case of the #3 pulse it is also to be expected since its amplitude is substantial due to the unvaryingly significant iliac reflection site.

Another subtle but very important detail is visible in the evolution of the arrival times of the component pulses during the Valsalva maneuver. The #3 pulse responds first to the rising pressure at the onset of Valsalva. Using the marker at 50 seconds on the graph, visual inspection establishes readily that both the arrival time of the #1 pulse as well as the BP line shapes measured with the Colins monitor move off their baseline well after the marker while the arrival time of the #3 pulse has responded well before (approximately 4 seconds before the Colins signals and the #1 component pulse).

The delayed reaction of the Colins signals and the #1 component pulse relative to the response of the #3 pulse is a result of the different Young's moduli of the involved arteries. In the absence of significant hardening of the central arteries (the subject in this case is a 46 year old runner in fit shape), the arterial walls in the arm, and in the arterial periphery in general, are significantly tougher than those of the central arteries, a well-known fact due to different elastin versus collagen content in the walls. Since a given rise in blood pressure will tend to distend the softest sections of the arterial tree first, it is entirely reasonable to expect the pulse propagation velocities of the central arteries to also increase first. Consequently one would expect the #3 pulse, which samples the entire aortic tree twice along its propagation path, to accelerate relative to the #1 pulse, which traverses essentially only the arm complex arteries that are characterized by significantly less compliant wall material. The same reasoning explains the time delay between the response of the #3 pulse and the onset of the Colins monitor, which measures its signal at the radial artery.

How the time delay between the #1 and the #3 pulse evolves as the pressure continues to rise is also determined by the differential Young's moduli of the arm and central arteries. In persons with "elastic" central arteries one observes the continued narrowing of the time delay between the #1 and the #3 pulse with rising pressure, indicating that propagation velocities the central arteries, due to their significantly higher distensibility, continue to change faster than those of the arm complex and the arrival time of the #3 pulse changes faster due to the much longer path length over which velocity changes can manifest themselves.

In persons with "hard" central arteries, the time delay between #1 and #3 is markedly different. In the case of "hard" central arteries the time delay between #1 and #3 increases with rising blood pressure. Since in this case the central arteries have very little excess distensibility relative to the arm, or peripheral, arteries, the arm arteries respond equally to a rise in pressure. However, due to the higher pulse velocity propagation and the higher gain of the pulse propagation velocity as a function of pressure in the arm versus the central arteries, the #1 pulse continues to accelerate away from the #3.

Remarkably, it is possible to observe an intermittent state of the evolution of the delay time between #1 and #3 in the same patient, that is, in the presence of continuously rising pressure, the delay time initially decreases, reverses, and then continues to increase. Clearly such patients have only some hardening of the central arteries as a result of which they exhibit the pressure onset behavior of patients with "elastic" arteries. The limits of "easy" distensibility are, however, quickly reached and the pressure load is increasingly shared by the peripheral, and specifically the arm, arteries as a result of which, for the same physical reasons that were given above, they exhibit the delay time behavior of "hard" artery patients at higher pressures.

Returning once more to the case of persons with "elastic" central arteries, the reversal of the delay time between #1 and #3 with increasing blood pressure may also occur in this case, but at a much higher pressure. Whether this effect exists, remains to be seen.

While the time evolution of T13 (time delay between pulse #3 and pulse #1) as well as the relative amplitude of P3 and P1 is comparatively straightforward, the time delay and amplitude evolution of the pulse relative to the P1 pulse is somewhat more complex. This is due to the fact that the P2 pulse has an additional degree of freedom relative to the P1 and P3 pulses in that its amplitude relative to the other two pulses changes with blood pressure, specifically pulse pressure. This point is perhaps more clearly made after first examining the amplitude evolution of the P3 and P1 peaks as a function blood pressure, specifically systole. The P3 pulse arises from the reflection site in the vicinity of the iliac arteries. This reflection is due to a combination of effects due to arterial bifurcations as well as changes in arterial diameter. Ageing effects, such as through the deposition of plaque, will also alter the reflection site, but these are long-term and slowly-varying effects. In contrast, the physical parameters of this reflection site are not likely to change appreciably with blood pressure. Put differently, the reflection coefficient of the site is not very pressure-dependent. Therefore, if the amplitude of P1 increases because the systolic blood pressure has increased relative to the diastolic floor, P3 should increase proportionally, or the ratio of P3/P1 should remain largely constant with changes in blood pressure. Observations to date have shown this to be the case.

Figure 10:
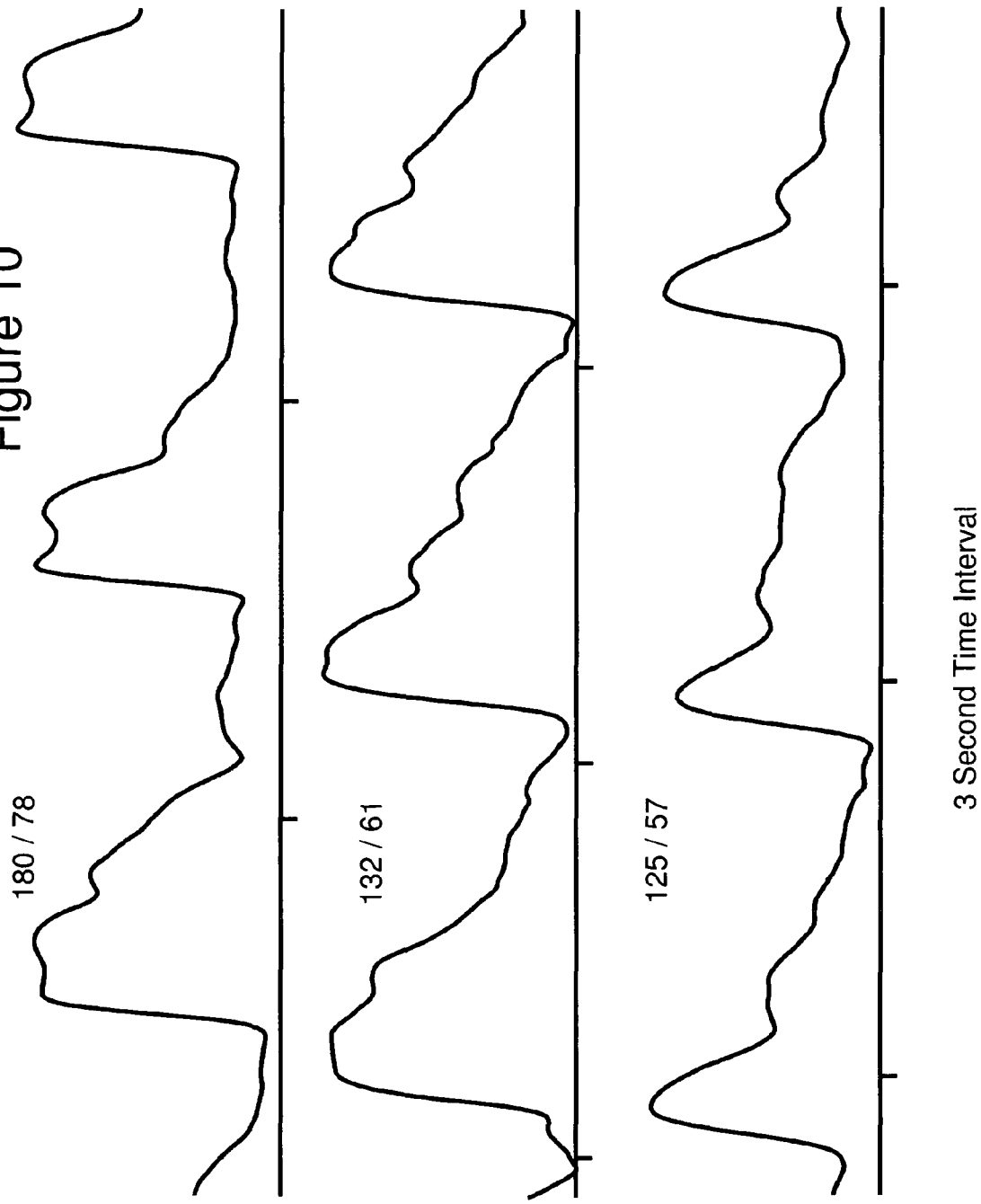
FIG. 10 shows radial pulse shape changes with dropping BP cuff readings.

In contrast to the amplitude response of P3, which maintains its proportionality to P1, the ratio of amplitudes P2/P1 increases proportionally with blood pressure. This is not surprising since the fact that the "second systolic peak" becomes very prominent in cases of high blood pressure is well known and readily observable. An example is shown in FIG. 10, which presents radial heartbeat samples from the same patient at significantly different blood pressures. The increased amplitude of the #2 pulse with increased blood pressure is clearly evident, and not surprising in view of the physical arguments given previously. The P2 pulse arises from the reflection site at the height of the renal arteries that is characterized by a diameter mismatch between the thoracic and the abdominal aorta. With increasing blood pressure the thoracic aorta's diameter increases and it does so at a faster rate than the abdominal aorta due to a difference in wall material strength. Consequently, the amplitude of the P2 pulse will increase at a different rate than the P1 with increasing blood pressure, that is, the ratio P2/P1 will increase. The increased amplitude of the P2 pulse will also modify its propagation velocity, which depends highly on the pulse's amplitude. The resulting non-linear delay time behavior, which is due to the fact that the pulse increasingly accelerates as its amplitude rises, can be observed in large-amplitude blood pressure variations such as are observed in dialysis patients.

A final consideration that completes the description of P2's temporal and amplitude evolution is the fact that its amplitude is actually proportional to pulse pressure, that is, the difference between systolic and diastolic pressure. This of course is also the case for P3, since it is only the pulsatile part of the blood pressure that can produce a reflection. In the case of P2, however, the fact that its amplitude changes relative to the amplitude of P1 gives rise to the interesting opportunity that the ratio of P2/P1 is a measure of the pulse pressure, self referenced within each heartbeat pulse and therefore largely independent of coupling efficiencies.

Model

Figure 6:
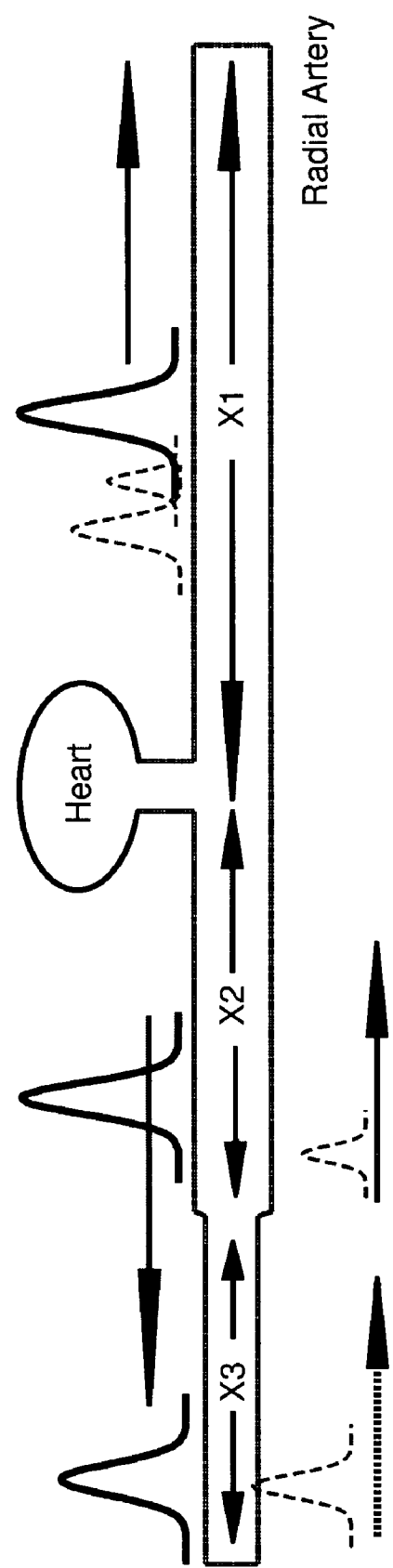
FIG. 6 shows a schematic of the radial arterial pulse path model.
Figure 7:
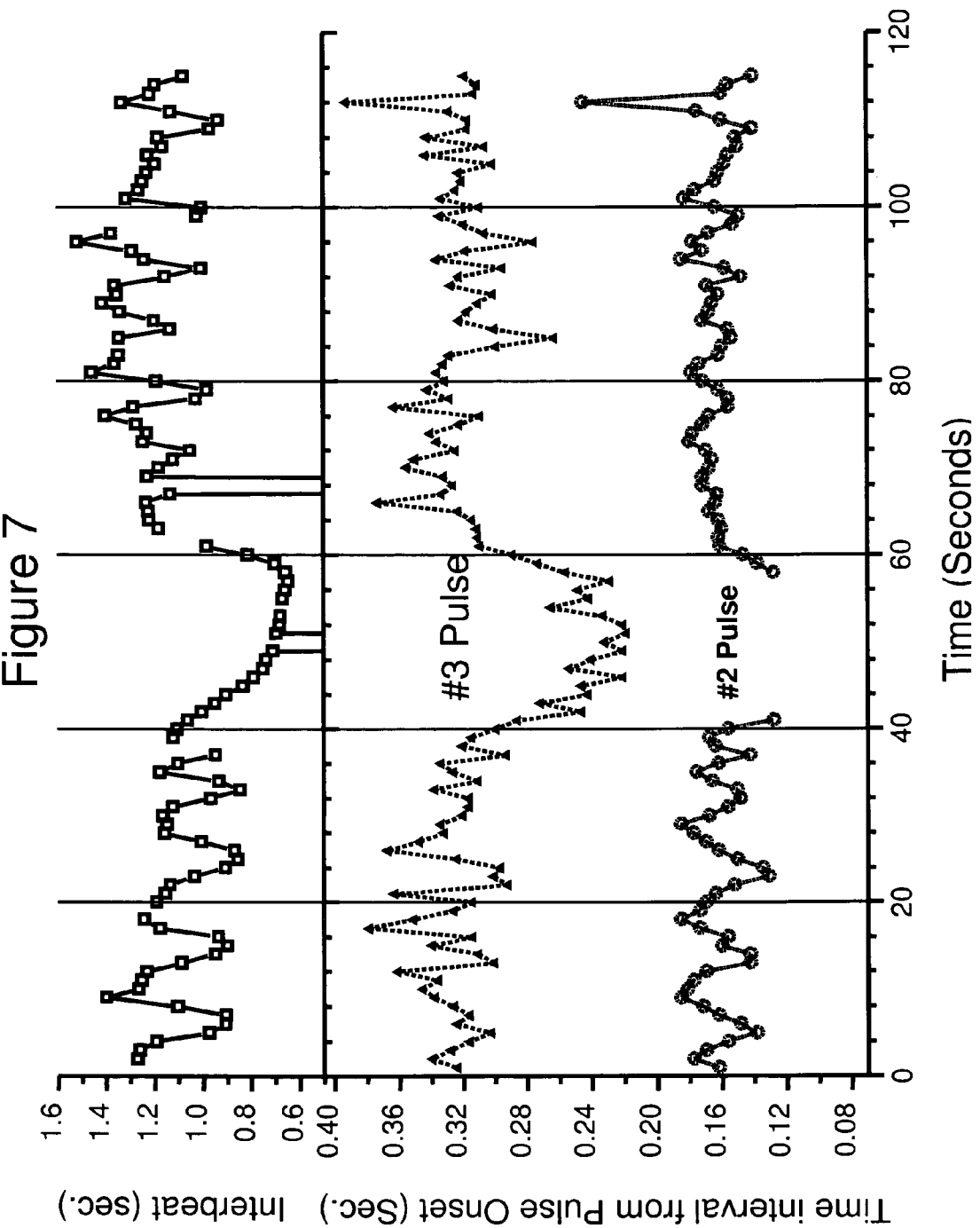
FIG. 7 shows graphs of the inter-beat interval and the time delay between composite pulses during Valsalva maneuver.

Based on the arterial pulse path model outlined in FIG. 6 it is now possible to construct a $$t_1 = \frac{x_1}{c_1(\ldots, P_{systole-RFL1*PulseP}, \ldots)}, \quad \text{(eqns. 1-4)}$$

$$\text{where } c_n(h_n, E_n, \xi_n, P_n, \alpha_n, \rho)$$

$$t_2 = \frac{x_2}{c_2(\ldots, P_{systole}, \ldots)} + \frac{x_2}{c_2(\ldots, P_{diastole+RFL2*PulseP}, \ldots)} + \frac{x_1}{c_1(\ldots, P_{diastole+RFL2(1-RFL1)PulseP}, \ldots)}$$

$$t_3 = \frac{x_2}{c_2(\ldots, P_{systole}, \ldots)} + \frac{x_3}{c_3(\ldots, P_{systole-RFL2*PulseP}, \ldots)} + \frac{x_3}{c_3(\ldots, P_{diastole+RFL3(1-RFL2)PulseP}, \ldots)} + \frac{x_2}{c_2(\ldots, P_{diastole+RFL3(1-RFL2)PulseP}, \ldots)} + \frac{x_1}{c_1(\ldots, P_{diastole+RFL3(1-RFL2)(1-RFL2)(1-RFL1)PulseP}, \ldots)}$$

$$t_4 = \frac{x_2}{c_2(\ldots, P_{systole}, \ldots)} + \frac{x_3}{c_3(\ldots, P_{systole-RFL2*PulseP}, \ldots)} + \frac{x_3}{c_3(\ldots, P_{diastole+RFL3(1-RFL2)PulseP}, \ldots)} + \ldots$$

linear model of the delay times with which the individual pulses will arrive at the radial artery.

In the above set of equations, $t_n$ refers to the arrival time of the nth pulse. The arterial path segments are defined as follows: n=1 corresponds to the arterial path from the aortic arch to the radial artery site, n=2 refers to the arterial path from the aortic arch to the renal arteries reflection site, essentially the thoracic aorta, and n=3 refers to the arterial path between the renal arteries reflection site and the iliac reflection site, essentially the abdominal aorta. As an example, the primary pulse, n=1, will traverse a part of the aortic arch, whose contribution to the pulse velocities is averaged in as it is part to all the path lengths, and will then traverse the arteries of the arm to reach the radial artery site, designated as x1, traveling at a pulse velocity that is largely in the pressure regime of systole. The functional relationship between pulse propagation velocity and blood pressure will at this point be described in a general form as $c_n(h_n, E_n, \xi_n, P_n, \alpha_n, \rho)$ where the parameter definitions are as follows: E is the Young's modulus, $\alpha$ is the artery's diameter, h is the arterial wall thickness, $\rho$ is the fluid density, $\xi$ is the arterial compliance and P is the pressure. With the exception of the fluid density of blood $\rho$ the arterial parameters are artery specific, as indicated by their subscript n. Furthermore, the Young's modulus and the arterial extensibility $\xi$ follow, as will be shown below, different functional relationships with regard to pressure. The pulse pressures in the various arterial path segments are also subject to the reflection coefficients (RFLn) at the various junctions of arterial segments. RFL1 refers to the reflection coefficient of the arterial junction between the aortic arch and one of the subclavian arteries while RFL2 and RFL3 refer to the renal arteries reflection site and the iliac reflection, respectively.

Referring again to the n=1 pulse as an example, the arrival time of the pulse at the radial artery site $t_1$ will be determined by the velocity $c_1$ which is subject to the systolic pressure minus the amplitude lost due to the transition from the aortic arch to one of the subclavian arteries. It is clear that a more detailed analysis of the pressure pulse's transition through the various arterial segmental interfaces in the arm can be included. Based on what has been learned modeling pulse transition times up to this point, these contributions appear not to be appreciable.

A description of the terms describing the path length of the "second systolic", or the n=2, pulse follows. It traverses the thoracic aorta ($x_2$) at systolic pressure, traverses is again as a reflection after re-direction at the reflection site of the renal arteries (indicated as percentage of pulse pressure determined by RFL2 plus diastolic pressure) and then enters the arm arteries where is loses another percentage of its amplitude due to arterial segment transition characterized by RFL1. Verbal descriptions of $t_3$, the delay time of the $3^{rd}$ pulse, the iliac reflection, and especially $t_4$, the delay time of the first re-reflection between the renal and the iliac reflection site become fairly involved. To enhance clarity, the terms in the equations describing different arterial path segments are arranged in the order that each described pulse traverses them, starting as a primary pulse and then as a reflection.

The next significant issue is the shape of the arterial velocity/pressure response curve or the functional form of $c_n(h_n, E_n, \xi_n, P_n, \alpha_n, \rho)$ for each of the three arterial path segments as they relate to the dominant pressure regime that the pulses comprising the radial pulse are subject to. Based on the results of numerous other researchers, starting with the work of Anliker, it is reasonable to assume that the general functional shape of the curve for any of the major arteries will be exponential. However, because the #2 and #3 pulses travel mostly at arterial pressures far below systolic pressure they sample by and large only the linear portion of the pressure/velocity response curve, in marked contrast to the velocity response curve of the #1 pulse, which demonstrates a pronounced exponential behavior.

Figure 11:
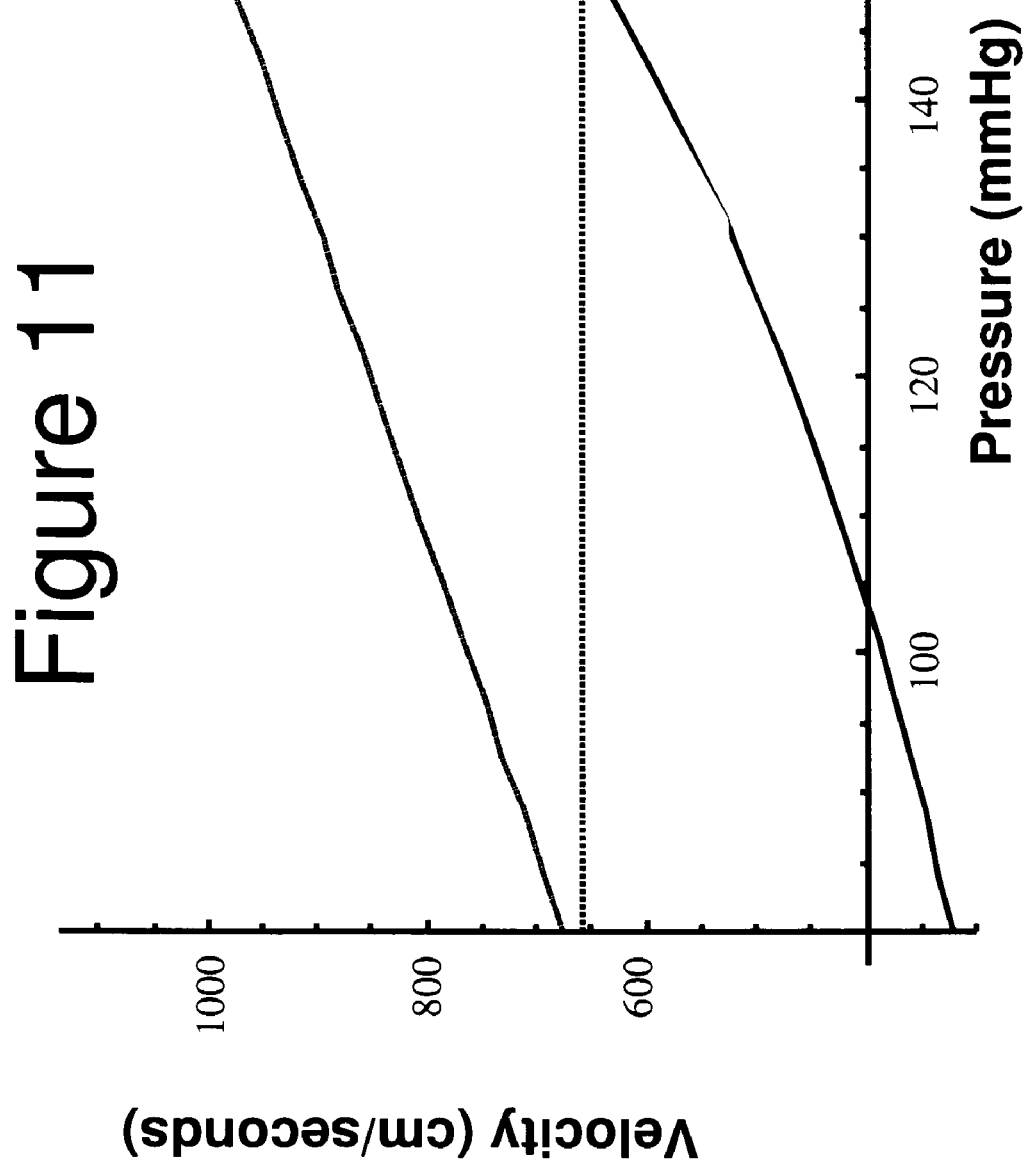
FIG. 11 shows the functional forms of the pressure-dependent velocity profile of constituent pulses 1-3 as a function of pressure.

To quantify the pressure/velocity response curve for each of the three primary pulses, the systolic and diastolic blood pressures measured with the Colin Pilot unit were correlated with the delay times of the three primary pulses. The resulting fitted functions are displayed in FIG. 11. The difference in velocity response, and therefore time delay response, between the different pulses is striking. While the #1 pulse demonstrates an exponential response curve, the #2 and #3 pulses' velocities follow a linear relationship. More importantly, the pulse propagation velocity of the abdominal aorta region exceeds that arm arteries, a result that is in line with values published in the medical literature. Of course this result holds for this subject who is a member of the "elastic" central arteries group. Results are quite different for "hard" central arteries patients, where arm pulse propagation velocities can reach 15 m/s and more due to the shift of pressure load from the hard central arteries to the arm complex arteries, as was explained above.

Figure 12:
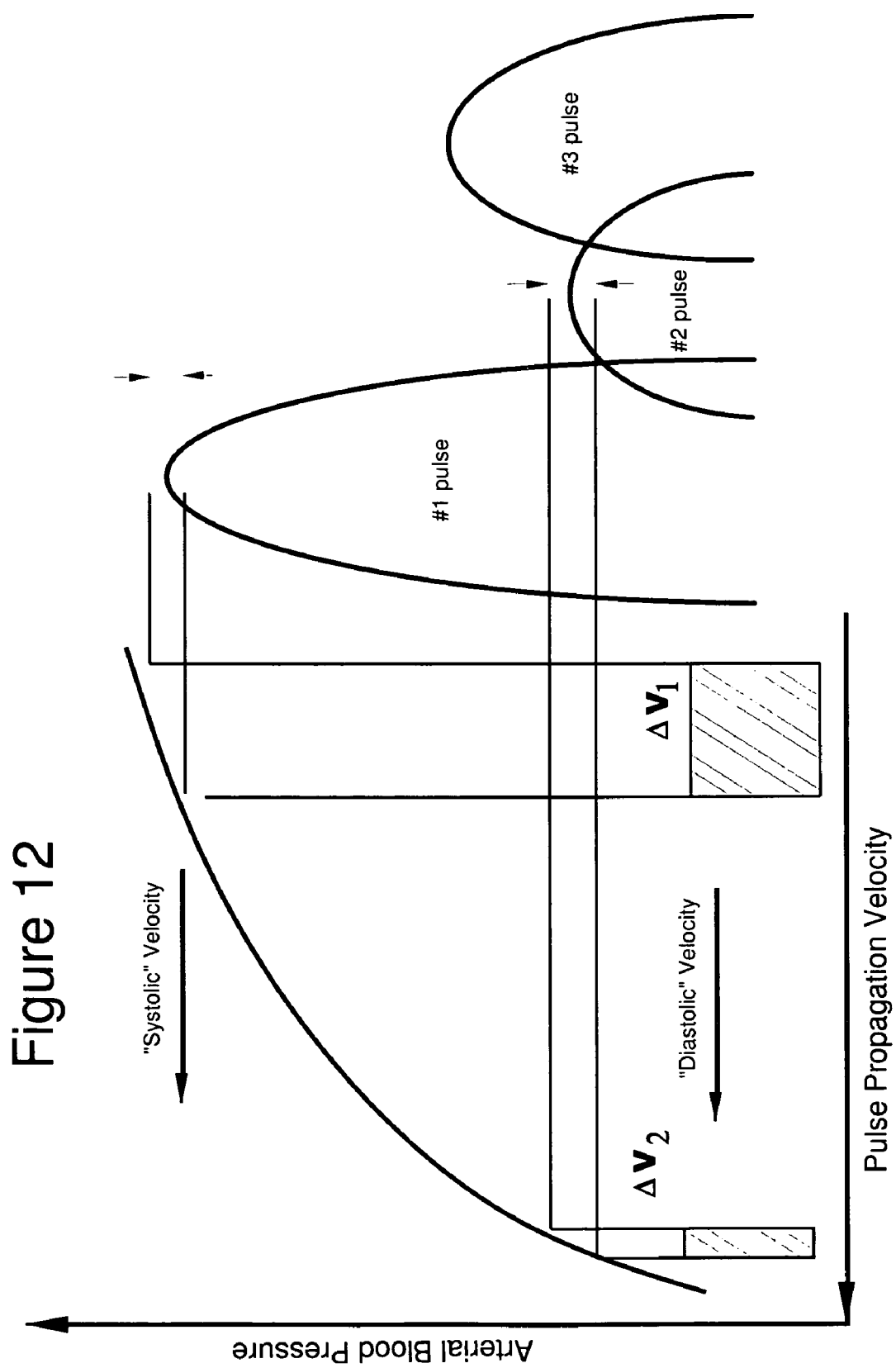
FIG. 12 shows the effect of small pressure variations on the propagation velocity of the three primary component pulses.

The behavior of the three pulses is summarized in FIG. 12. While the #1 pulse samples the top of the systolic pressure regime throughout its travel along the arterial tree to the radial pulse site, the #2 and #3 pulses do so only on the initial traversal of sections of the aorta, spending a much greater part of their propagation time in significantly lower blood pressure ranges. As a result the, presumably exponential, pressure/velocity relationship that governs their travel as outward bound primary pulses is masked by the linear pressure/velocity relationship that governs their travel as reflected pulses. More importantly, differential changes in travel time between the different pulses can be resolved because of the different functional forms and gains of the velocity curves that govern the propagation of the different component pulses. As an example, for a diastolic pressure of 75 mmHg and a systolic blood pressure of 130 mmHg (RFI1=RFI2=10%, RFI3=30%, x1=55 cm, x2=43 cm, x3=35 cm, 0.94*10^6 dyne/cm²), pulse #2 traverses sections x2, x2, x1 in 68, 87, and 126 milliseconds, respectively, spending 76% of its travel time in the pressure regime relatively close to diastole. For Pulse #3 the comparable time values for the path segments (x2, x3, x3, x2, x1) are (68, 67, 85, 84, 119 milliseconds). It should be noted that the #3 pulse traverses the arm faster than the #2 pulse did because it travels, due to the higher iliac reflection, at a higher pressure and therefore higher velocity). Consequently, the #3 pulse spends about 70% of its time at pressures significantly lower than systole. Since the #2 pulse spends most of its transit time in the softest part of the arterial system, the aortic arch, and the thoracic aorta, it is not surprising that its pressure/velocity response curve is the flattest, again keeping in mind that this patient has soft central arteries.

Specifically, the functional forms for the velocity functions of the three arterial sections that $$c_1(\xi_1, p(R_{Rfl1})) = \sqrt{\frac{h_1 E_{1o} e^{\xi_1 p}}{2\rho\alpha_1}},$$

$$c_2(\xi_2, p(R_{Rfl1}, R_{Rfl2})) = \sqrt{\frac{h_2 E_{2o}}{2\rho\alpha_2}} + \xi_2 p,$$

$$c_3(\xi_3, p(R_{Rfl1}, R_{Rfl2}, R_{Rfl3})) = \sqrt{\frac{h_3 E_{3o}}{2\rho\alpha_3}} + \xi_3 p$$

(eqns. 5-7)

have been used in the analysis thus far are:

The equation for the pulse propagation velocity of pulse #1, $c_1$, is a slightly modified version of the equation known as the Moens-Korteweg equation which takes into account the non-linearity of the Young's modulus. It is understood that other functional forms may be found to be more suitable for describing the arterial pressure/velocity response as the number of analyzed data increases. While it is clear that the pulse propagation velocity depends on all the arterial parameters listed, including $h_n$, and $\alpha_n$, the primary variables are the pressure and the slope of the pressure/velocity curve. Since the pulse pressure is highly dependent on the different reflection coefficients, the dependence has been made functionally explicit in the expressions.

Underlying the model at its present state of sophistication is a number of implicit assumptions, the first of which is the assumption of average systemic systolic and diastolic pressures in the major arteries. However, this assumption is reasonable as it is well known that the systemic pressure does not drop more than a few percent until the artery/arteriole interfaces, which are characterized by pressure drops of tens of mmHg. It is also well known that the pressure pulse increases in amplitude and accelerates as it heads to the arterial periphery due to the arterial taper and changes in arterial wall composition. These effects are not yet included in the model but it is clear that they would simply modify the functional dependencies. The predictive value of the model will determine the degree to which a more sophisticated description of the artery is required. Another issue is the stability of the $\xi$ factors under dynamic conditions. The pressure/velocity response curve of a given arterial section will likely change under certain physiological conditions. For instance it has been shown in experiments involving patients wearing pace makers, which make it possible to isolate the effect of changing the heart rate without other physiological effects such as changes in blood pressure etc, that pulse velocity increases with heart rate. The physical mechanism that has been suggested is the fact that the artery effectively stiffens because the time for the arterial wall to recoil between passing pressure pulses is diminished. It may be necessary to include the effect in the model once it has been further characterized.

Figure 13:
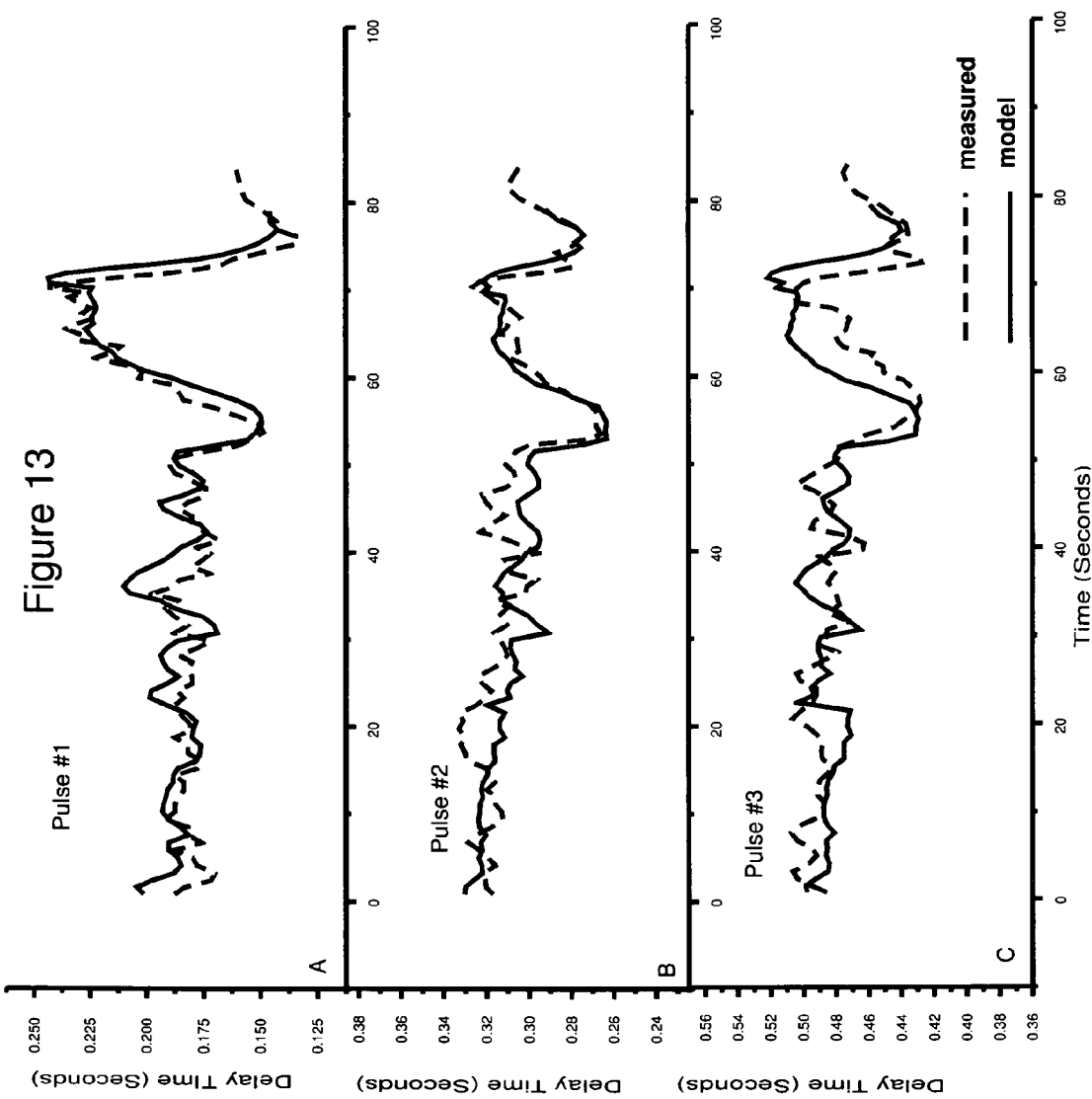
FIGS. 13a, b, c, show comparisons of the model's predictions with experiment.

FIGS. 13a, 13b, and 13c, which present predicted and measured time delay curves for the three primary pulses, give a sense of the agreement between the two. The predicted delay time values were obtained by isolating the diastolic and systolic peak-to-peak blood pressure values obtained from the Colin unit and inserting them into the model. The agreement of the range of delay time values is no surprise since correlations were used to relate the blood pressures measured with the Colin unit to the measured pulse delay times. Encouraging, is the fact that the overall time evolution of the predicted and measured delay times agrees well.

A different set of data was collected from a patient undergoing dialysis. The procedure is very invasive, involving the removal and re-insertion of a significant fraction of a patient's blood volume, and large blood pressure variations are common. This patient's blood pressure spiked immediately after hook-up to 180/78 mmHg and then progressively decreased over the course of the next 80 minutes toward the patient's normal baseline of about 113/55 mmHg. FIG. 10 shows pulse shapes collected at different times during the decay of blood pressure. Several pulse shape features stand out that indicate both the state of this patient's core arterial system as well as the dynamic change in blood pressure. One feature is the early return of the tail of the pulse amplitude to baseline. As a result of the hardening of the arteries this patient's reflected waves all have increased velocities, decreasing diastolic perfusion and increasing pulse pressure, a characteristic that becomes more and more prevalent with age and, especially, with diabetics.

While the early return of the tail pulse amplitude to baseline is a feature common to all the shown pulse shapes, other features of the front of the pulse clearly appear to be related to the change in blood pressure. One is the profound change in amplitude (and delay time, as the following analysis will demonstrate) of the "second systolic" (#2) peak, which clearly decays as the blood pressure drops, dramatically changing the overall shape of the pulse. Furthermore, the relative timing of the three primary component pulses is clearly different for the different blood pressure states, as a result of which the overall pulse shape is "bunched up" in the low blood pressure case while clearly covering a larger temporal extent in the high BP situation. Finally, the rise time of the front end of the primary, systolic pulse undergoes clearly visible changes as BP changes, with the top of the primary pulse receding temporally from the onset as the blood pressure drops.

Figure 14:
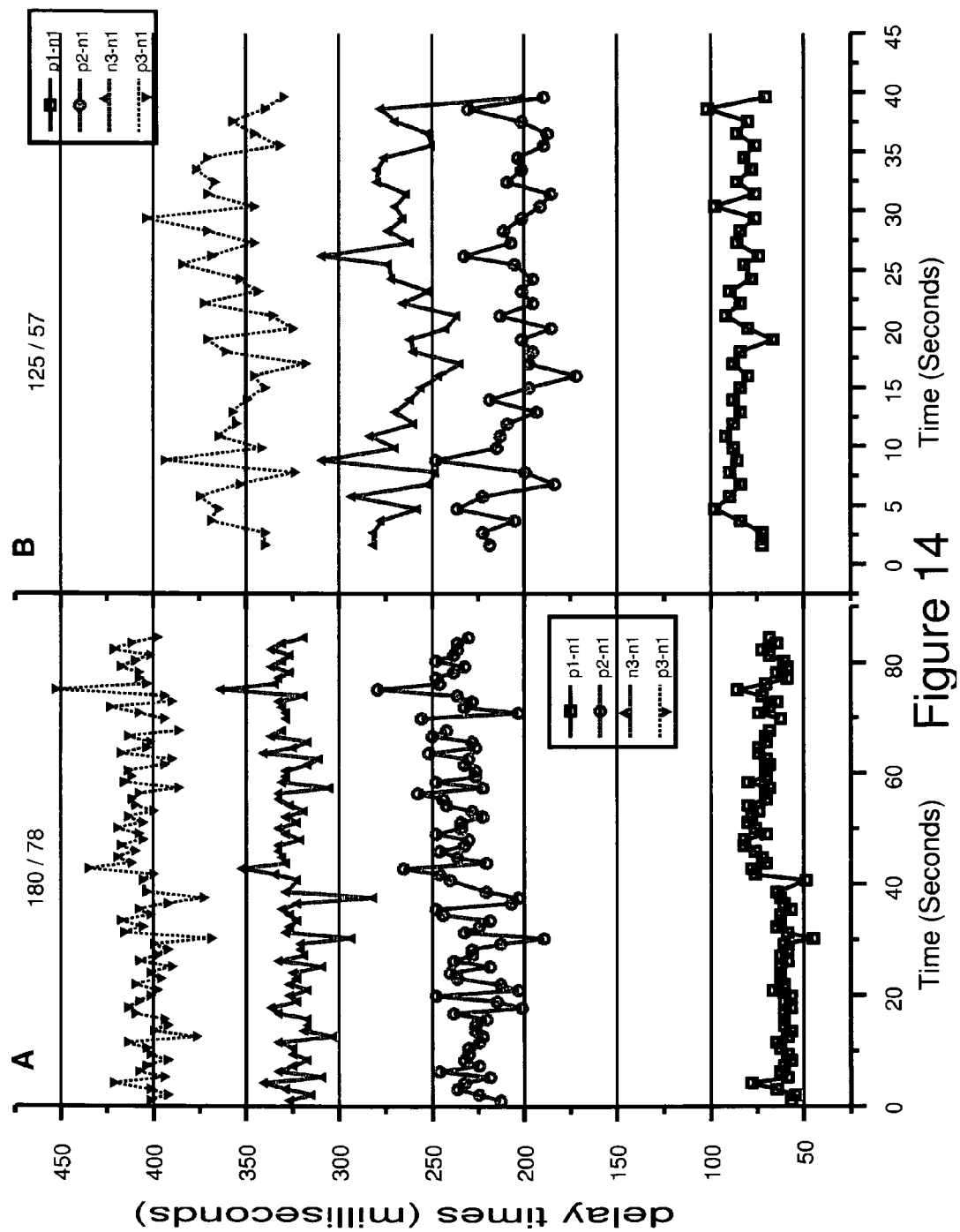
FIG. 14 shows the delay times of the three component peaks, as well as the minimum between P2 & P3, relative to the pulse onset, for cuff pressures indicated.

FIG. 14 presents a more quantitative comparison of the pulse delay times in the high (180/78, left graph) versus low blood pressure (125/57) case. Shown are the delay times, in units of milliseconds, of the #1, #2, and #3 pulses as well as the minimum between the #2 and #3 pulse relative to the onset of the primary (#1) pulse for a duration of 1.5 minutes (left) and 40 seconds (right graph). One observation is the fact that the separation of the pulses, particularly that of the #1 pulse relative to the subsequent pulses, is significantly larger in the high blood pressure case. Similarly, the time delays between the #2 and #3 pulse have shrunk. These temporal changes, relative to the onset of the pulse, are significant, involving time delay changes in excess of 50 milliseconds.

These observations are expected based on the proposed component pulse model of the radial arterial pulse and identify this patient as having significant hardening of the central arteries. Therefore the #1 pulse, traveling at the highest (systolic) pressure and sampling the most non-linear part of the arterial velocity/pressure response, will see the most significant diminution in velocity as the pressure drops, decelerating more strongly than the following two primary pulses. The delay time between the other pulses will also change as a function of pressure because their amplitudes depend on the reflection coefficients of the reflection sites, renal and iliac, that gave rise to those reflected pulses. Strictly speaking, the #3 pulse should be traveling faster because the iliac reflection site is usually more dominant (35-40%) compared to the renal reflection site (10-20%). However, because of the tremendous change in the amplitude of the #2 pulse, which must be related to changes at the reflection site, the #2 pulse additionally accelerates because the increased pressure amplitude increases its pulse propagation velocity.

Figure 15:
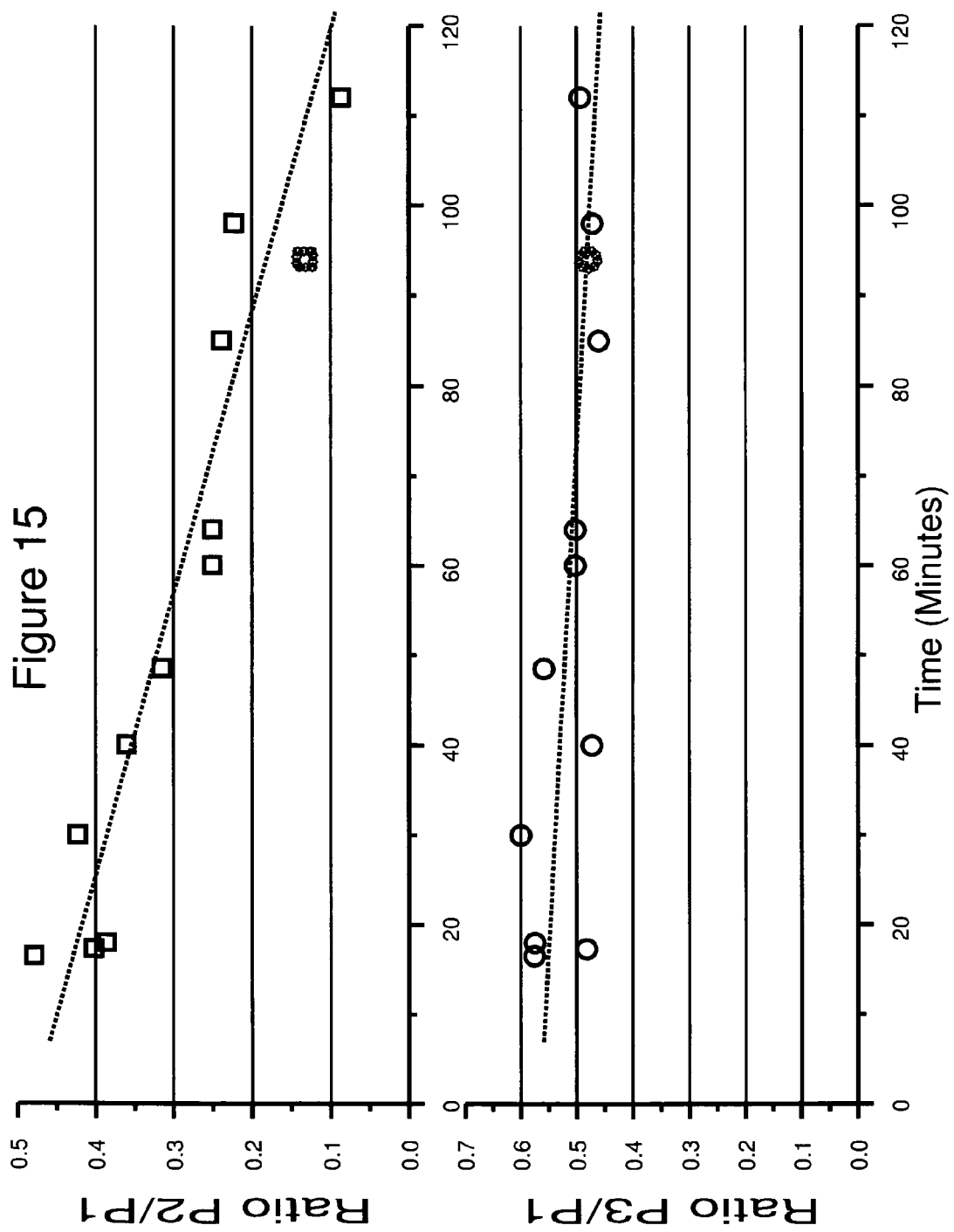
FIG. 15 shows changes in the amplitude ratios P2/P1 (top) and P3/P1 during the patient's BP decay.

FIG. 15 presents the ratios of the amplitudes of the #2 pulse to that of the #1 pulse and that of the #3 pulse to that of the #1 pulse as a function of time. Individual data points represent averages of 20 heartbeat pulses. The obvious observation is that the #2/#1 amplitude ratio changes appreciably during the decay of blood pressure while the #3/#1 amplitude ratio remains essentially constant. Keeping in mind that the #2 pulse reflection originates at the site where the aorta undergoes a sizable diameter change, it is clear that the reflection site must change as a function of blood pressure, specifically systolic. The likely scenario is that the softer-walled thoracic aorta, in contrast to the harder-walled abdominal aorta, increasingly distends with increasing systolic pressure, as a result of which the impedance mismatch of the junction to the propagating arterial pulse increases, giving rise to a reflected #2 pulse whose amplitude, relative to the amplitude of the primary peak, is dependent on systolic pressure.

Figure 16:
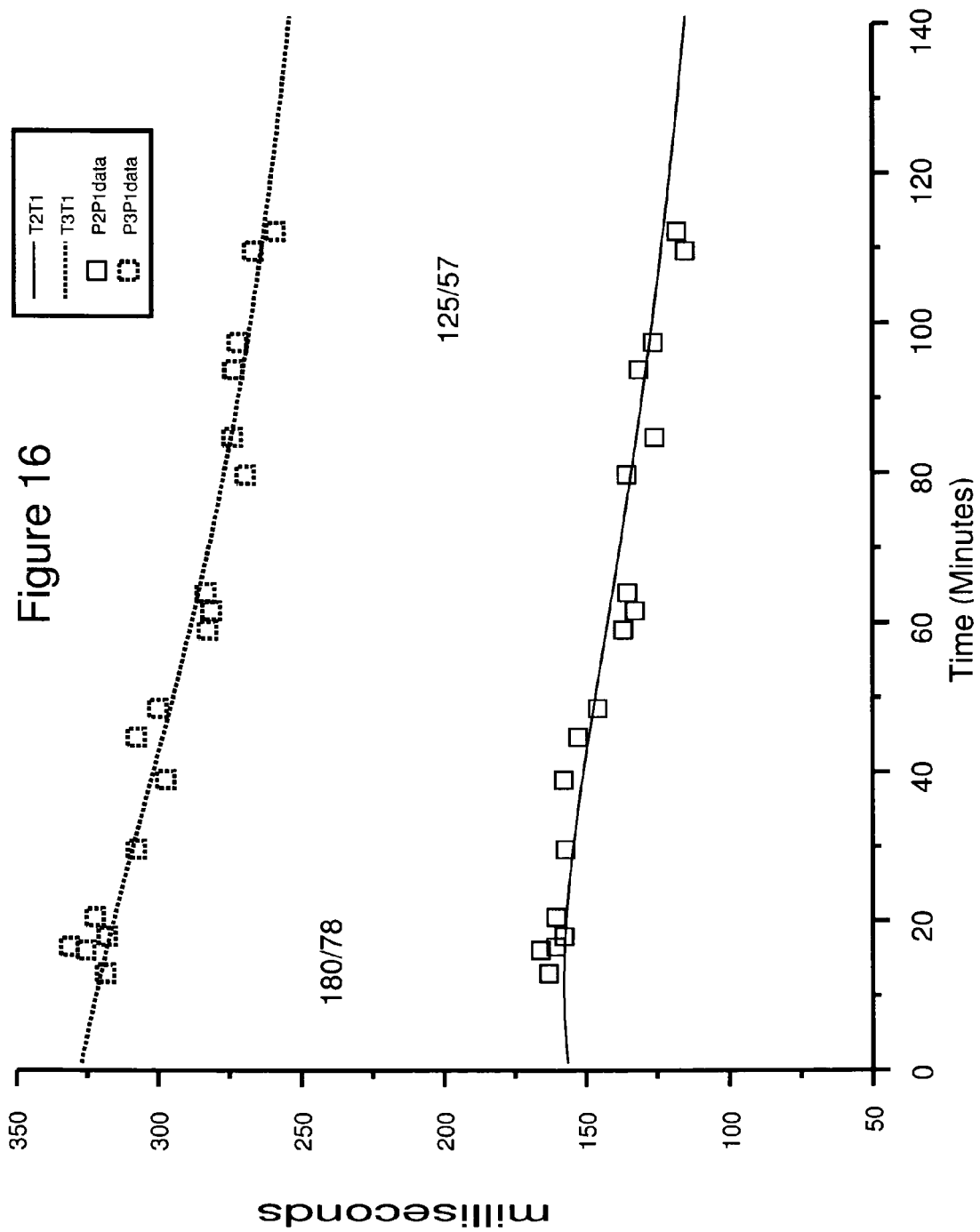
FIG. 16 shows the delay time prediction and data for T12 and T13 as a function of systolic & diastolic pressures, which are functions of time.
Figure 17:
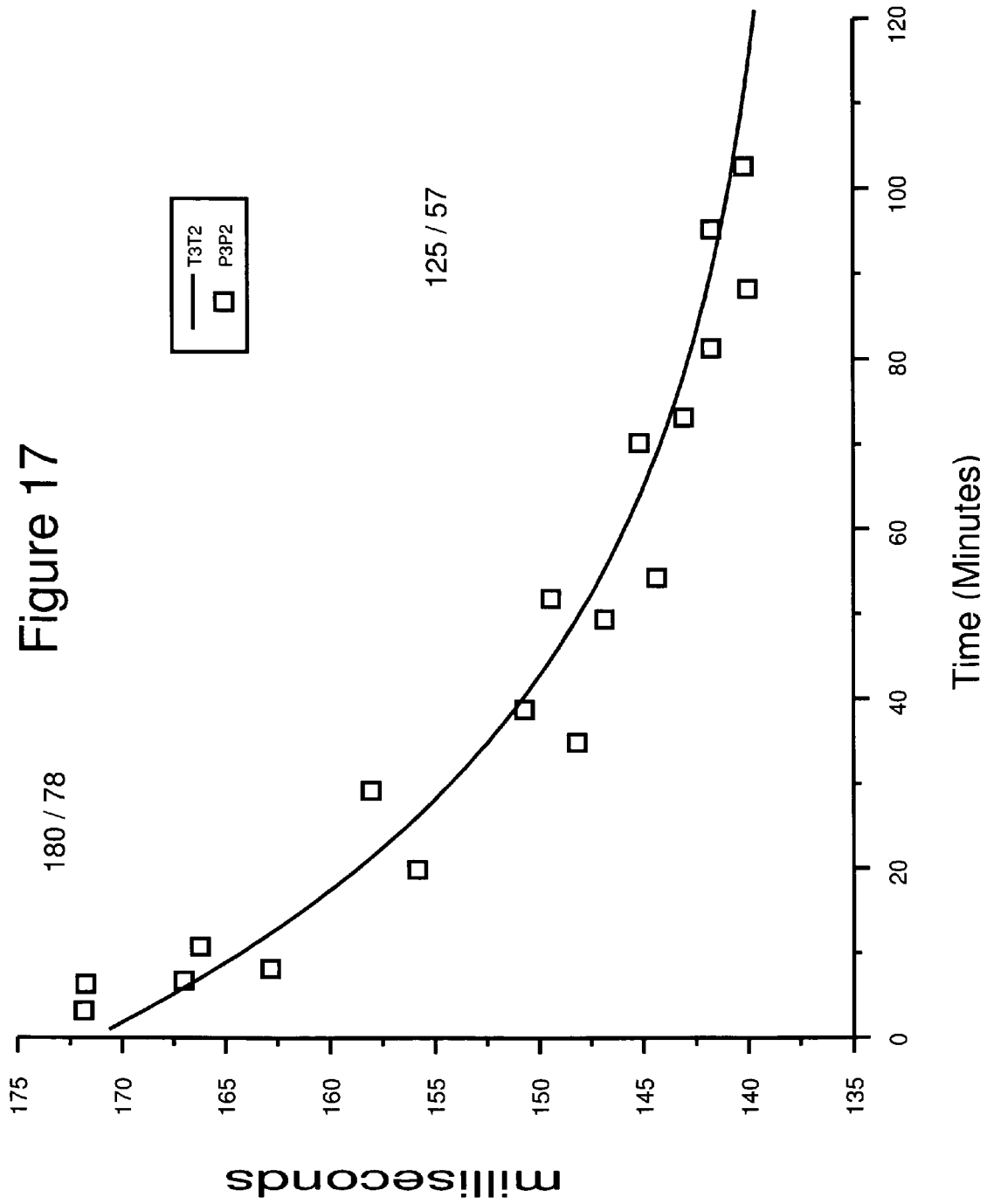
FIG. 17 shows the delay time prediction and data for T23 as a function of systolic & diastolic pressures, which are functions of time.
Figure 18:
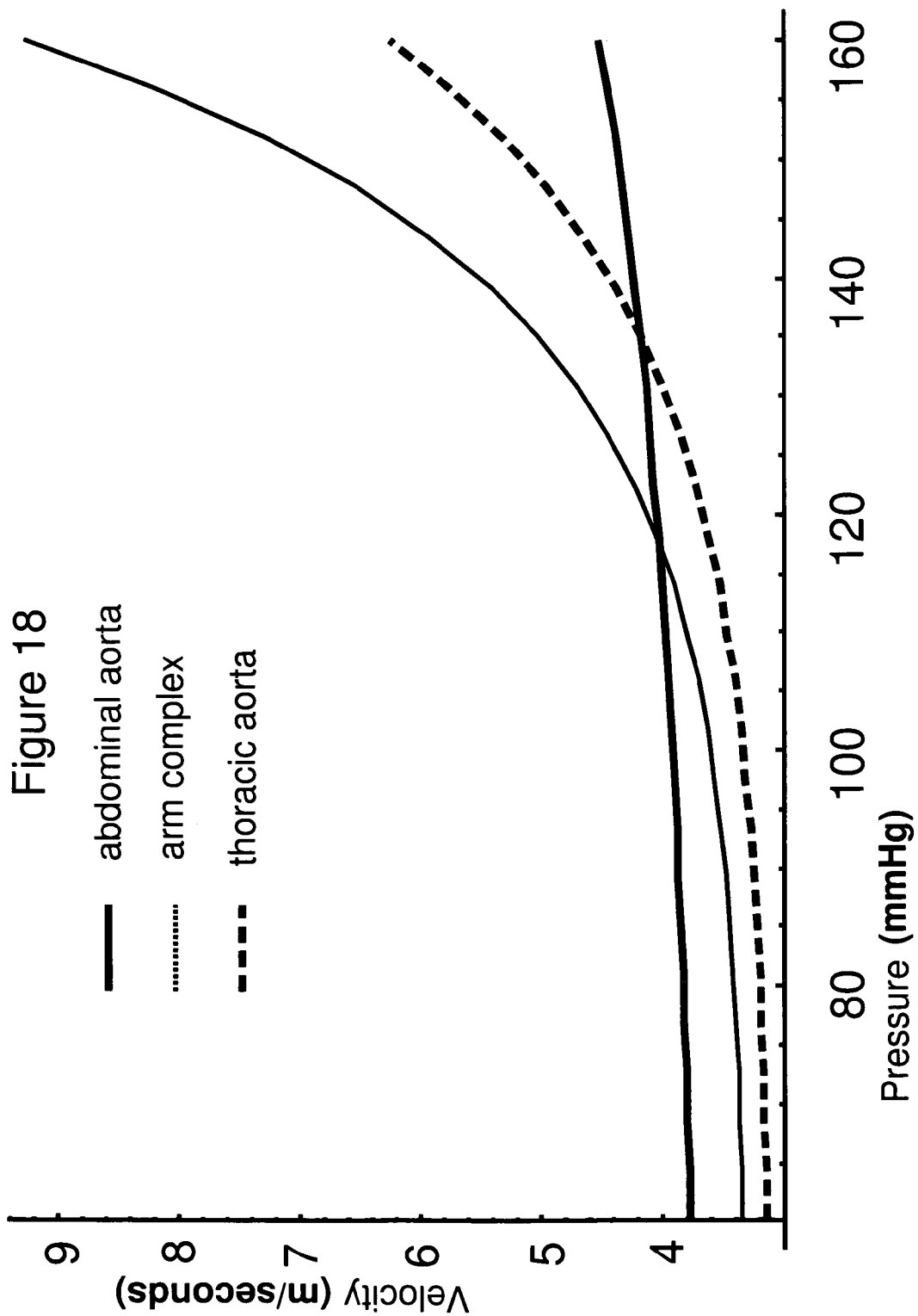
FIG. 18 shows the arterial velocities of the principal path sections as a function of pressure as determined by the model.
Figure 19:
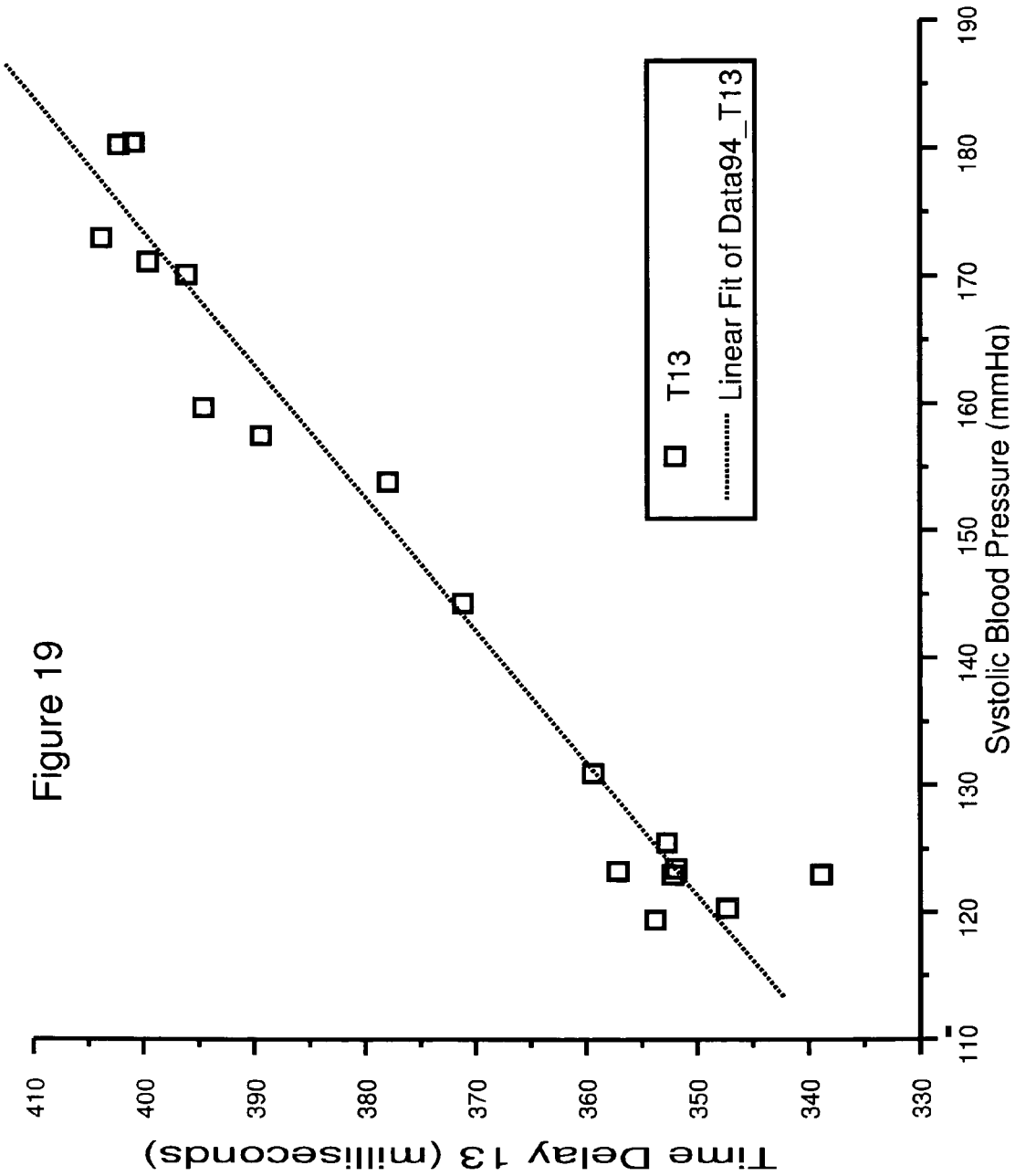
FIG. 19 shows the P3-P1 (T13) delay as a function of systolic blood pressure.

FIGS. 16 and 17 summarize some of the quantitative results as function of time at the blood pressures indicated and present the best predictions for the delay times between pulses #3-#1 (T13) and #2-#1 (T12) and pulses #3-#2 (T23). The horizontal axis is time but the predictions of the model as a function of time incorporate the clinically recorded systolic and diastolic blood pressures. Of particular interest is the obvious non-linearity during the first 20-40 minutes of the high pressure period. The model incorporates a pressure-dependent reflection coefficient R2 for the renal site, based on the results presented in FIG. 15. It is clear from the behavior of the delay curves in this realm that, as the #2 pulse gained in amplitude due to the increased reflection coefficient, it accelerated relative to the #1 pulse, shortening the delay time between the two pulses. The increased #2 amplitude is clearly missing in the amplitude of the #3 pulse, which as result decelerated relative to the #1 pulse. The predicted non-linearities in the delay time response are clearly born out in the data. FIG. 18 presents the velocity/pressure response curves that the model used to calculate the time delays between the different component pulses. The distinct near-linear pressure response of the of the delay time between the #1 and the #3 pulse (T13) can be observed in FIG. 19 which present T13 as function of systolic blood pressure.

Description of Method

In what follows the procedure for obtaining blood pressure values from the delay times of the composite pulses is described.

From the discussion above is clear that the delay time T13, which is the delay time between the primary pulse #1 and the iliac reflection #3, provides a direct measure of systolic blood pressure variations. In contrast to the #2 peak, whose amplitude, proportional to the other component peaks, is highly pressure-dependent, the #3 peak's amplitude largely retains its proportionality with the #1 peak due to the stability of the iliac reflection site. For reasons explained above, T13 increases or decreases as a function of rising systolic blood pressure depending on the state of hardening of the central arteries, which, for purposes of monitoring patients on a day-to-day basis, is a constant. One method to establish whether the correlation of T13 with systolic pressure is positive or negative is to monitor the amplitude of the #2 peak. Its amplitude has a positive correlation with systolic pressure, i.e. it always rises with increasing pressure. Based on the current information future statistical analyses of large data sets of delay times will establish that it is also possible to predict, based on delay times corrected for sex, height and age, which correlation is likely to be correct.

While the systolic pressure is determined using T13, the pulse pressure is tracked by monitoring the ratio of the amplitudes of the #2 and the #1 pulse, i.e. P2/P1, which rises monotonically with pulse pressure. The starting values for correlating P2/P1 with pulse pressure are however very different for different patients since the ratio is small for patients with "hard" central arteries (on the order of 0.04), and larger (0.2) for patients with "elastic" central arteries at comparable normal blood pressures. Patients with hard central arteries tend to have, at normal blood pressures, diminished P2 amplitudes, which increase dramatically with rising blood pressure. Patients with "elastic" central arteries tend to have very pronounced P2 amplitudes at resting blood pressures, indicating that their thoracic aortas are significantly more distended than patients with "hard" central arteries at comparable blood pressures. This observation is supported by published results that demonstrated a drop in aortic pulse propagation velocities by about 10% in subjects who changed from a sedentary lifestyle to one characterized by endurance exercise training. The effect, which was demonstrated to be entirely reversible with cessation of exercise, was shown to be due to a change in aortic distensibility.

With the blood pressure extremes determined, the mean arterial pressure is then determined by obtaining the ratio of the integral over the line shape of the full radial arterial pulse to the time interval over which the integral is performed, a standard procedure.

It is clear from the above example and the previous discussion of the influence of the reflection sites on the component pulse amplitudes that, by comparing ratios of the relative amplitudes of the three (or more) component pulses, the relative magnitudes of the renal and iliac reflection site coefficients, or RFL2 and RFL3, can be determined. The reflection coefficient associated with the interface between the arterial junction between the aortic arch and one of the subclavian arteries, RFL1, has to be determined independently and in the present analysis it has been simply set to 10%. However, its influence on the analysis is minimal since its effect is common to all pulse paths. In addition the RFL1 coefficient is, similarly to the reflection coefficient RFL3 associated with the iliac reflection site, not likely to change except over significant time frames that allow for relatively slow physiological processes such as, for example, the deposition of atherosclerotic plaque to take place.

It is also clear that the effectiveness of implementing the model presented above depends entirely on the efficiency of the algorithms that are used to detect a. the individual radial heart beat pulses and b. the composite pulses that comprise the radial pressure pulse shape. One approach to detect the heartbeat pulses as well as the composite pulses will now be described in detail. It is understood that a plethora of different approaches are available to accomplish the same tasks.

Implementation

Figure 20B:
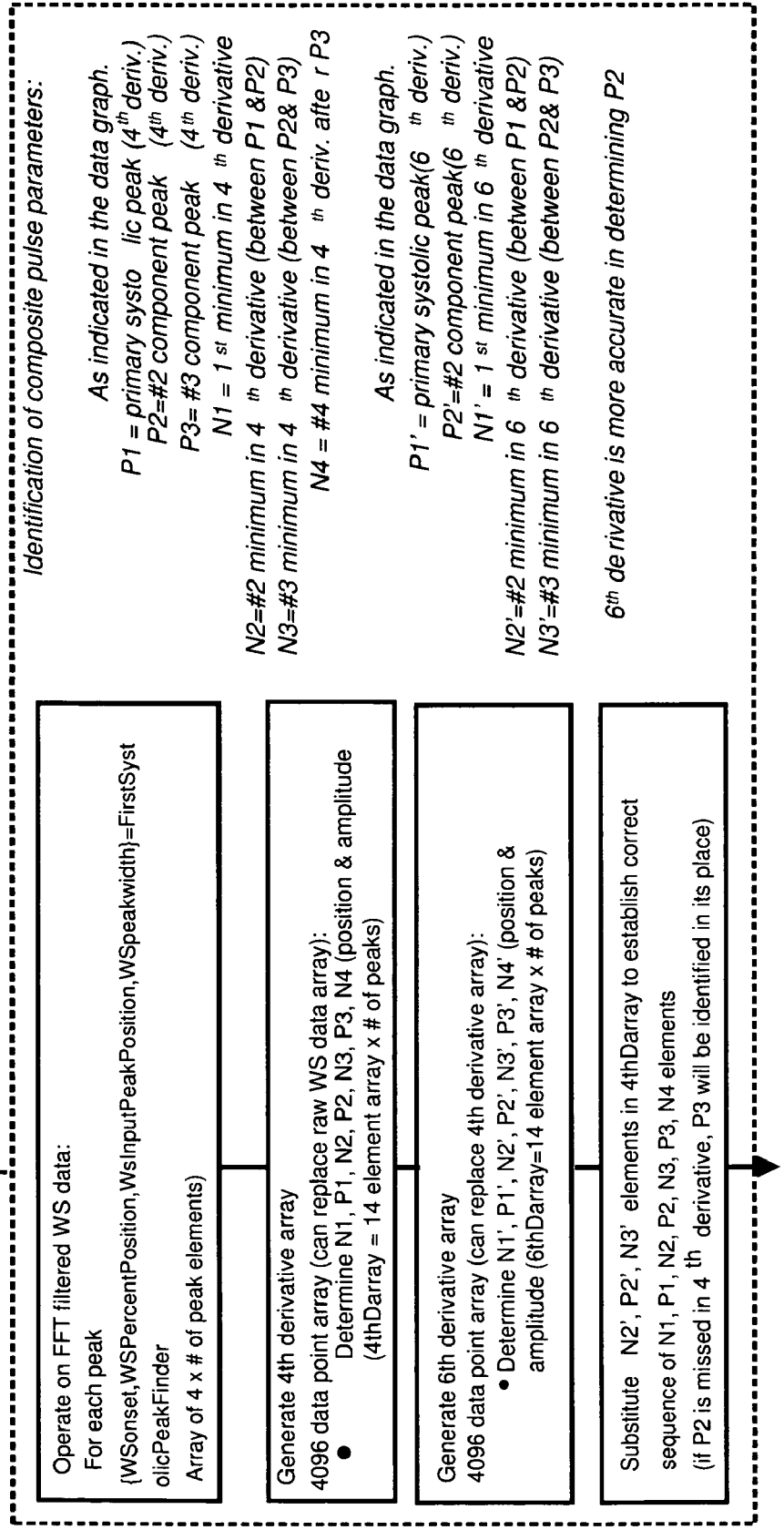
FIGS. 20a, b, and c, show the flow chart of the algorithmic approach, with the sequence being from 20a, to 20b, and then to 20c.

The following description is made with reference to the flow chart shown in FIG. 20. The preferred method is one where a data stream of the radial arterial pulse signal is collected at 512 Hz from a sensor that produces a signal proportional to the arterial pulse pressure. The choice of using an acquisition rate that is a power of 2 facilitates using Fourier transform analysis (FFT) to filter the data and to make spectrally sensitive determinations as to its fidelity.

A further convenient method is to collect the data in a rolling 8-second long buffer that is processed at whatever update rate is deemed convenient. Eight seconds is again a convenient choice because it allows effective FFT filtering with sufficient resolution. Processing longer time windows increases the likelihood that disruptive events, such as arm movements, will compromise part of the data section to be processed.

The first task is to identify the heart beats in the signal stream in order to perform calculations on them. Presently, this is accomplished as follows:

An FFT bandpass filter (0.5-20 Hz) removes all dc offsets and centers the data approximately around zero.

The positive/negative variance of the signal, relative to its mean, is determined.

Peaks are found by using an offset comparison relative to a rolling average.

The initial number of peaks is then down-selected by examining each peak according to the following conditions:

The zero-crossings of the onset slope of each heart beat in the signal are determined by finding the correct slope range:
  the desired onset slope of each heart beat pulse is
   Positive (as opposed to the negative slope of the tail of the pulse)
   Sustained (noise spikes can produce any slope, but not over a time interval significant in duration relative to the heart beat pulse duration)
   Usually higher and more sustained than the positive slope associated with the incisura portion of the heartbeat
The difference between the maximum and minimum of a given peak is compared to the background signal.
The separation between adjacent peaks is compared to physiologically relevant minimal interbeat interval and, once it becomes available as part of subsequent repetitive processing, the actual inter-beat interval of the subject.

With the time location of the onset of the individual radial heartbeat pulses determined, the detection of the composite pulses can proceed. A method that has been found to be very useful is to take sequential derivatives of the radial pulse line shape. It is a standard method that is used extensively in situations where the aim is to identify multiple convolved peaks, such as spectroscopy or astronomy. This technique is very useful in this context because, based on the arguments given, the radial pulse is a convolution of five component pulses subject to the high-frequency (low pass) filtering of the arterial tree during its propagation from the heart to the arterial periphery. Sequential differentiation increasingly resolves the component pulses. This is particularly the case in the #2 pulse, which very often is discernible only as a slight broadening of the #1 pulse. Care has to be taken, since derivatives amplify high-frequency noise, to filter and/or smooth the data between separate applications of differentiation. There is a certain amount of trial and error involved because excessive filtering or smoothing will distort the arterial pulse line shape while insufficient filtering and smoothing will cause the resulting line shapes to be obliterated with noise. In the analysis so far rolling averages over 20 data points, corresponding to about 40 milliseconds of data at an acquisition rate of 512 Hz, have been used with satisfactory results.

Specifically the $4^{th}$ and $6^{th}$ derivatives are used. The choice of an even derivative is obvious because it yields a line shape that is symmetric with the original pulse. The #1 and #3 pulses are readily resolved in the $4^{th}$ derivative. The $6^{th}$ derivative is frequently necessary because the #2 peak cannot be fully resolved in the $4^{th}$ derivative. An example is given in FIG. 21 in the first peak. While the #2 peak can be visualized in the $4^{th}$ derivative, it is very challenging to quantify its position or amplitude while the $6^{th}$ derivative readily resolves the peak. Care has to be taken when using derivatives to determine amplitudes, however, because the amplitude represents a rate that is proportional to the inverse of the acquisition rate with which the data was recorded. Furthermore it is important to realize that the $6^{th}$ derivative produces peaks that are 180 degrees out of phase with the $4^{th}$ derivative, that is, a peak in the $4^{th}$ derivative will correspond to a valley in the $6^{th}$ derivative.

With the differentiations complete, a zero-slope-finding routine is used to find the positions of the peaks and valleys in the $4^{th}$ derivative and $6^{th}$ derivative pulse spectra (see FIG. 21). In the $6^{th}$ derivative, only the #2 pulse's position, width, and amplitude are determined. It is important to keep in mind that the $6^{th}$ derivative is inverted relative to the $4^{th}$ derivative, i.e. peaks in the $4^{th}$ derivative are valleys in the $6^{th}$ derivative. The end result is a an array of positions, as indicated in FIG. 21, labeled N1, P1, N2, P2, N3, P3, N4 along with their respective amplitudes from which the most important time differences (T13=P3−N1, T12=P2−N1) are calculated. In the context of the derivatives, and only in this context, P1 and N1 are essentially synonymous except for an offset. The reason is that the time difference between N1 and P1 in the derivatives is entirely dominated by the onset of the pulse, which is largely insensitive to changes in blood pressure. Changes in blood pressure do significantly change the onset time of the pulse but those changes occur largely in the top third or fourth of the onset, a section whose effect is swamped in the derivative representation by the enormous curvature change of the invariant bottom onset of the pulse.

The pulse amplitude of P1 is determined using the actual pulse signal, but the position of P1 is determined using the first derivative. The reason for doing so is that the close proximity of P1 and P2 often obscures the exact position of P1, which is the maximum of the systolic peak. The easiest case is that of P2 having a small amplitude, in which case P1 is clearly resolved (FIG. 10, bottom graph). More common is a situation where the P2' amplitude is appreciable, as a result of which a double-peaked plateau results in place of P1's distinct maximum. Older patients with sufficiently hardened arteries and consequently increased pulse velocities will display an "augmentation index" where P2 is sufficiently big and arrives sufficiently early after P1 to cause P1 to be a shoulder before the so-called "second systolic peak". Middle-aged athletes will also have significant P2 amplitudes due to their elastic thoracic aortas, as a result of which P1 and P2 can form a complexly convoluted line shape. Using the first derivative and the width of the primary pulse, which corresponds to the complete rise time of the original pulse onset, it is possible to obtain a reliable measure of the position of the primary peak #1 under widely varying arterial conditions.

The ratio of P2/P1 is calculated using the positions and amplitudes obtained in the $6^{th}$ derivative since comparison of amplitudes across derivatives is challenging because both the width of a peak as well as its amplitude is affected by the order of the derivative. The ratio P3/P1 is calculated using original data but positional information obtained in the first derivative, in the case of P1, and the $4^{th}$ derivative in the case of P3.

With the extraction of the set of parameters from the data complete, a number of physiological life signs parameters can now be determined, among them heart rate, breathing rate, systolic blood pressure, and diastolic blood pressure.

The heart rate is easiest since it simply involves converting the inter-beat interval between adjacent heartbeats into a rate which can be accomplished beat by beat or as an average over any desired number of inter-beat intervals. It is of course also possible to study longer time windows of inter-beat intervals, such as is done in heart rate variability studies which involve the generation of power spectra of time windows ranging from 5 minutes or 24 hours.

With regard to determining the breathing rate the pulse decomposition analysis is particularly suitable because, as the data in FIG. 8 presented in demonstrates, the T12 interval or the P2/P1 interval are particularly susceptible to the blood pressure-modulating effects of respiration. In the case of harder central arteries, the transmural pressure modulation across the wall of the thoracic aorta due to respiration produces pulse propagation velocity variations in the arm artery complex as well as the thoracic aorta. Due to the arteries' different distensibilities, there is a differential difference between two velocity variations as a result of which T12 changes with the periodicity of respiration. In the case of soft central arteries, the thoracic aorta's diameter changes significantly, as a result of which R2, the reflection coefficient at the height of the renal arteries changes. By the arguments previously given, P2/P1 changes, accordingly, with respiration.

Different methods are then available to extract the breathing rate from the series of T12 intervals or P2/P1 ratios. The simplest employs a threshold detector to determine the periodicity of the modulations. More sophisticated methods employ spectral methods. Care, however, has to be taken because the time positions of the heart beats, and consequently of the T12 and P2/P1 values, are spaced unevenly. Standard methods, such as interpolating the data points onto an evenly spaced time grid or employing a Lomb-Scargle periodogram approach, are available to implement them.

As was previously explained, T13 and the trend in P2/P1 are used to determine the systolic blood pressure component. The correlation between T13 and systolic pressure appears to be essentially linear (in the example of the patient on dialysis the coefficient was 0.96 mmHg/milliseconds with an offset of 233.4). Different patients are likely to have different coefficients which however will probably be categorizable according to height (longer arterial pathways will lengthen time intervals, sex (females tend to have lower arterial pulse velocities than males), fitness (studies have demonstrated the correlation between decreased aortic pulse velocities and increased fitness as quantified by increased oxygen consumption as a result of endurance exercise training), normal or pathological hardening of the central arteries relative to the peripheral arteries, as well as other factors yet to be determined.

As explained before, the correlation between T13 and systolic pressure has been observed to be positive, negative, and in one patient, it reversed with increasing pressure. It is therefore important to track the trend in the P2/P1 ratio, which has a strictly positive correlation with systolic pressure. Furthermore, the algorithm requires a starting value for systole in order to determine the offset. Supplying several systolic pressure values such that the algorithm can determine associated delay time values is preferred because it permits the algorithm to calculate the correlation factor.

With the systolic pressure determined using T13, the pulse pressure is tracked by monitoring the ratio of the amplitudes of the #2 and the #1 pulse, i.e. P2/P1, which rises monotonically with pulse pressure. The starting values for correlating P2/P1 with pulse pressure are however very different for different patients as the ratio is small for patients with "hard" central arteries (on the order of 0.04) and larger (0.2) for patients with "elastic" central arteries at comparable normal blood pressures. The correlation between P2/P1 and pulse pressure also appears to be essentially linear (in the example of the patient on dialysis the coefficient was 0.76 mmHg/milliseconds with an offset of 22.36). A starting value for systolic and diastolic blood pressure is required in order for the algorithm to be able to determine the starting correlation between pulse pressure and the P2/P1 ratio.

Figure 22:
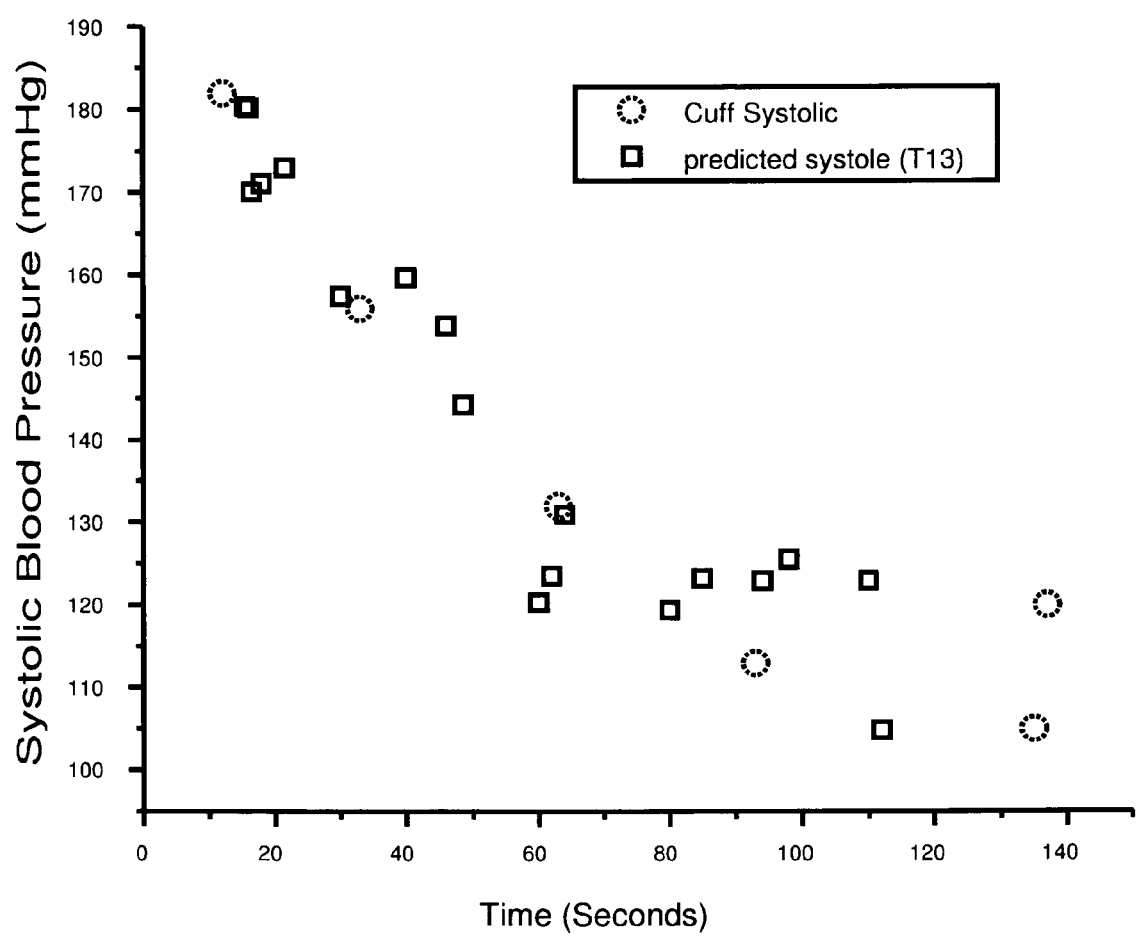
FIG. 22 shows systolic blood pressure readings obtained with an automatic cuff (circles) and results determined using the pulse-decomposition analysis.
Figure 23:
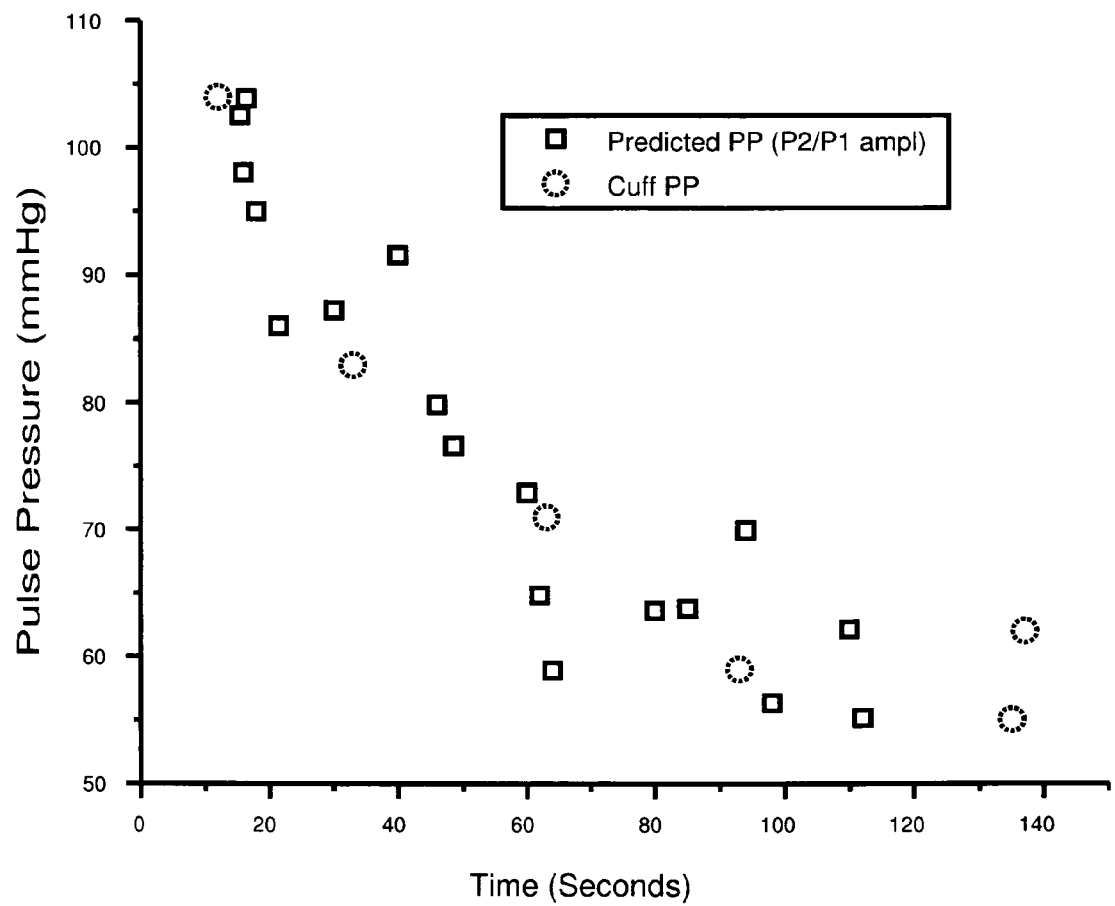
FIG. 23 shows pulse pressure (systolic-diastolic) readings obtained with an automatic cuff (circles) and results determined using the pulse-decomposition analysis.

FIGS. 22 and 23 give an example of the resulting overlap of the results for systolic pressures and pulse pressures (systolic-diastolic) recorded with an automatic cuff (open circles) as well as the predictions based on the pulse-decomposition analysis.

With the blood pressure extremes determined, the mean arterial pressure is then determined by obtaining the ratio of the integral over the line shape of the full radial arterial pulse to the time interval involved a standard procedure.

The articles cited above, are incorporated by reference:
1 McDonald DA: Blood flow in arteries, $4^{th}$ ed., London, 1998, Arnold, pp. 177.
2 Latham, RD et. al, Regional wave travel and reflections along the human aorta: a study with six simultaneous micromanometric pressures. *Circulation* 72, 1985, 1257-69.
3 Kriz J. et al, Force plate measurement of human hemodynamics, http://arxiv.org/abs/physics/0507135.

Broad Scope of the Invention:

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to."

In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example".

What is claimed is:

1. A method of determining physiological life signs using a non-invasive phlethysmograph having a heartbeat pulse sensor and a memory component, comprising the steps of:
   a) bringing a heartbeat pulse sensor of a phlethysmograph into contact with the surface of a patient's skin at point proximate an artery,
   b) measuring with said heartbeat pulse sensor at least one of arterial blood vessel displacement and blood pressure changes,
   c) collecting from said heartbeat pulse sensor a first data stream of measurements of step (b) and storing said data stream of measurements of step (b) within a memory component,
   d) extracting from a set of parameters from the collected data stored within said memory component, a number of physiological life signs parameters,
   e) calculating delay time between a primary systolic pulse and an iliac reflection pulse,
   f) calculating pulse blood pressure from said calculation of the delay time between the primary pulse and the iliac reflection,
   g) repeating steps (b) through (f) continuously for a predetermined period of time and collecting in a memory component a second data stream of measurements of the delay time between the primary pulse and the iliac reflection, and
   h) calculating pulse blood pressure variations from said data stream of measurements of the delay time between the primary pulse and the iliac reflection.

2. The method of claim 1, further comprising the steps of:
   i) calculating a ratio of an integral over a line shape of a full arterial pulse to a time interval, and
   j) determining mean arterial blood pressure from the ratio of the integral over the line shape of the full arterial pulse to the time interval.

3. The method claim 1, wherein said sensor produces a signal proportional to the arterial pulse pressure and said data stream is of radial arterial pulse signals from said sensor.

4. The method of claim 3, wherein said data is collected in a rolling long buffer on the order of about 5 to 20 seconds that is processed at a predetermined update rate.

5. The method of claim 1, wherein said sensor responds to blood pressure changes.

6. The method according to claim 1, wherein said sensor responds to arterial blood vessel displacement.

7. The method of claim 1, wherein said physiological life signs comprise at least heart rate, breathing rate, systolic blood pressure, and diastolic blood pressure.

8. The method of claim 1, further comprising monitoring a ratio of amplitudes of a second systolic pulse to the primary systolic pulse and determining blood pressure from said monitored ratio.

9. The method of claim 7, wherein said physiological life sign is breathing rate, and wherein breathing rate is determined by pulse decomposition analysis.

10. The method of claim 7, wherein said physiological life sign is respiration, and wherein the respiration is determined from a T12 interval, T13 interval, or P2/P1 ratio, wherein:
   pulse #1 is the primary systolic pulse,
   pulse #2 is a second systolic pulse,
   pulse #3 is the iliac reflection pulse,
   T12 is the delay time between pulses #2 and #1,
   T13 is the delay time between pulses #3 and #1,
   P2 is the amplitude of pulse #2,
   P1 is the amplitude of pulse #1, and
   P2/P1 is calculated using positions and amplitudes obtained from a pulse envelope.

11. The method of claim 7, wherein said physiological life sign is systolic blood pressure, and wherein a trend in a P2/P1 ratio is used to determine systolic blood pressure, wherein:
   pulse #1 is the primary systolic pulse,
   pulse #2 is a second systolic pulse,
   P2 is the amplitude of pulse #2, and
   P1 is the amplitude of pulse #1.

12. The method of claim 7, wherein said physiological life sign is mean arterial pressure and wherein mean arterial pressure is determined by obtaining a ratio of an integral over a line shape of a full radial arterial pulse to a time interval involved.

13. The method of claim 1, further comprising determining heart rate by converting an inter-beat interval between adjacent heartbeats into a rate beat by beat, or as an average over a predetermined number of inter-beat intervals.

14. The method of claim 1, further comprising
   i) removing all dc offsets from said data of step c, centering said data at approximately a zero value, and
   j) determining physiological life signs from said data.

15. The method of claim 14, wherein said dc offsets are removed and the data is centered at approximately zero by means of an FFT bandpass filter.

* * * * *